(12) United States Patent
Zhang et al.

(10) Patent No.: US 10,898,180 B2
(45) Date of Patent: Jan. 26, 2021

(54) HEART VALVE REPAIR METHOD

(71) Applicant: Hangzhou Valgen Medtech Co., Ltd., Zhejiang (CN)

(72) Inventors: Tingchao Zhang, Zhejiang (CN); Weiwei Zhang, Zhejiang (CN); Chunyuan Zhou, Zhejiang (CN); Xianzhang Zheng, Zhejiang (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 128 days.

(21) Appl. No.: 16/051,218

(22) Filed: Jul. 31, 2018

(65) Prior Publication Data
US 2019/0029671 A1 Jan. 31, 2019

(30) Foreign Application Priority Data

Jul. 31, 2017 (CN) .......................... 2017 1 0640936
Jun. 8, 2018 (CN) .......................... 2018 1 0588221

(51) Int. Cl.
*A61B 17/04* (2006.01)
*A61F 2/24* (2006.01)
(Continued)

(52) U.S. Cl.
CPC ...... *A61B 17/0487* (2013.01); *A61B 17/0469* (2013.01); *A61B 17/0625* (2013.01);
(Continued)

(58) Field of Classification Search
CPC .......... A61F 2/24; A61F 2/246; A61F 2/2466; A61F 2/2463; A61F 2/2427; A61B 17/04;
(Continued)

(56) References Cited

U.S. PATENT DOCUMENTS 5,423,857 A * 6/1995 Rosenman ........... A61B 17/064 411/457
5,456,400 A * 10/1995 Shichman ............ A61B 17/064 227/176.1

(Continued)

FOREIGN PATENT DOCUMENTS

CN 103251464 A 8/2013
CN 103826570 A 5/2014
(Continued)

OTHER PUBLICATIONS

International search report dated Oct. 11, 2018 from corresponding application No. PCT/CN2018/096901.
International search report dated Aug. 21, 2019 from corresponding application No. PCT/CN2019/087886.

*Primary Examiner* — Vi X Nguyen
(74) *Attorney, Agent, or Firm* — Hauptman Ham, LLP

(57) ABSTRACT

The present disclosure provides a heart valve repair method, comprising: advancing a distal end of a suture implanting apparatus from an outside of a body through a transapical approach into a left ventricle or a right ventricle of a heart; holding each leaflet of a heart valve with the distal end of the suture implanting apparatus; implanting at least one suture into the leaflet; withdrawing the suture implanting apparatus from the body; advancing a distal end of a suture locking apparatus from the outside of a body through a transapical approach into the corresponding left ventricle or the corresponding right ventricle; using the suture locking apparatus to lock the plurality of sutures; and withdrawing the suture locking apparatus from the body. The heart valve repair method has a simple surgical procedure, a low degree of patient trauma, and a high success rate of surgery.

6 Claims, 23 Drawing Sheets

(51) Int. Cl.
*A61B 17/062* (2006.01)
*A61B 17/00* (2006.01)
*A61B 17/29* (2006.01)

(52) U.S. Cl.
CPC .......... *A61F 2/2412* (2013.01); *A61F 2/2427* (2013.01); *A61B 2017/00243* (2013.01); *A61B 2017/00349* (2013.01); *A61B 2017/00783* (2013.01); *A61B 2017/0406* (2013.01); *A61B 2017/0409* (2013.01); *A61B 2017/0417* (2013.01); *A61B 2017/0464* (2013.01); *A61B 2017/0472* (2013.01); *A61B 2017/0488* (2013.01); *A61B 2017/0496* (2013.01); *A61B 2017/2926* (2013.01); *A61B 2017/2933* (2013.01); *A61B 2017/2937* (2013.01); *A61F 2/2457* (2013.01); *A61F 2220/0075* (2013.01)

(58) Field of Classification Search
CPC . A61B 17/0469; A61B 17/0401; A61B 17/08; A61B 17/10; A61B 17/0487; A61B 2017/0409; A61B 2017/00243
See application file for complete search history.

(56) References Cited

U.S. PATENT DOCUMENTS

| | | | |
|---|---|---|---|
| 7,335,213 | B1 | 2/2008 | Hyde et al. |
| 2013/0110230 | A1 | 5/2013 | Solem |
| 2015/0134057 | A1 | 5/2015 | Rourke et al. |

FOREIGN PATENT DOCUMENTS

| | | |
|---|---|---|
| CN | 104248457 A | 12/2014 |
| CN | 104367351 A | 2/2015 |
| CN | 104665888 A | 6/2015 |
| CN | 104939949 A | 9/2015 |
| CN | 105246431 A | 1/2016 |
| CN | 107468378 A | 12/2017 |
| CN | 107569301 A | 1/2018 |
| CN | 108186163 A | 6/2018 |
| CN | 109199468 A | 1/2019 |
| WO | 2017066888 A1 | 4/2017 |

\* cited by examiner

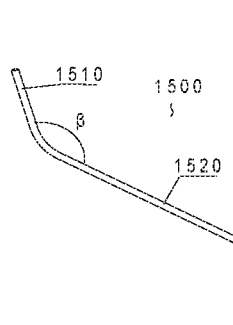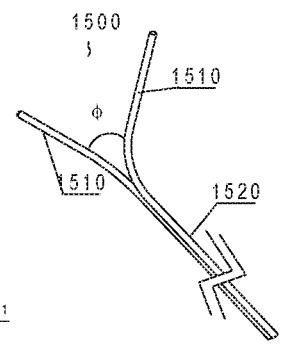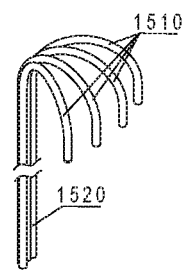
FIG. 14a     FIG. 14b     FIG. 14c
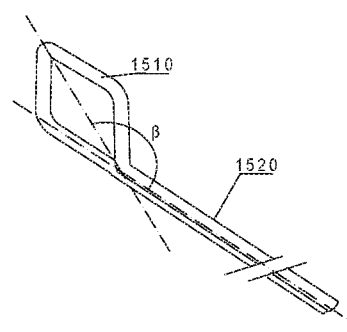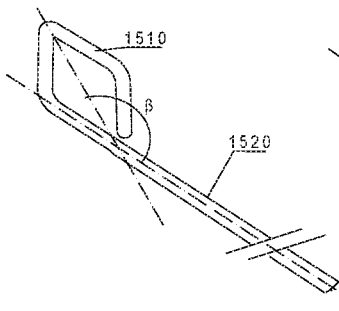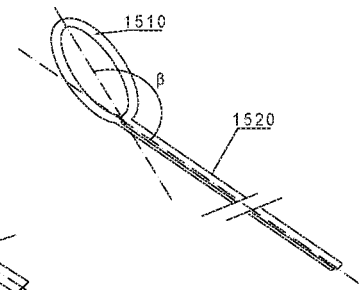
FIG. 14d     FIG. 14e     FIG. 14f
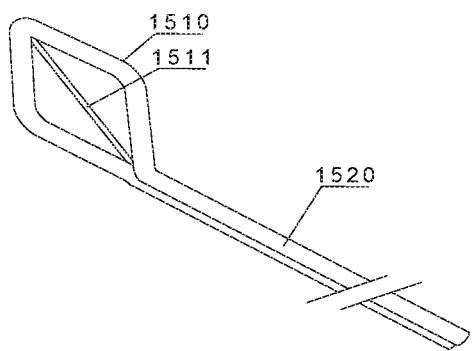
FIG. 14g

HEART VALVE REPAIR METHOD

TECHNICAL FIELD

This disclosure belongs to a field of medical appliances, and relates to a method for repairing a heart valve defect, and in particular relates to a heart valve repair method.

BACKGROUND

A mitral valve is a one-way "valve" between a left atrium and a left ventricle that ensures blood flow from the left atrium to the left ventricle. The mitral valve consists of two valve leaflets, an anterior leaflet and a posterior leaflet. When the left ventricle is in a diastolic state, the anterior leaflet and the posterior leaflet are apart from each other, and the blood flows from the left atrium to the left ventricle. When the left ventricle is in a contracted state, the chordae tendineae are stretched to ensure that the leaflets will not be washed by the blood flow to a side of the left atrium. FIGS. 1a and 1b show a normal healthy mitral valve with the anterior leaflet and the posterior leaflet closed to ensure blood flow from the left ventricle through an aortic valve to an aorta. The mitral valve shown in FIG. 2a and FIG. 2b has lesions. When the left ventricle is in the contracted state, the mitral valve cannot return to a close state as in a normal state, and the momentum of the blood flow will further cause the leaflet to fall into the left atrium, causing blood regurgitation, called "mitral valve regurgitation". Similarly, a tricuspid valve ensures blood circulation from a right atrium to a right ventricle. When the tricuspid valve cannot return to a close state as in a normal state, "tricuspid regurgitation" occurs.

At present, surgically implanted sutures or edge-to-edge repair are used to treat mitral regurgitation or tricuspid regurgitation. All these surgerys require invasive thoracotomy and general anesthesia, moderate hypothermic cardiopulmonary bypass as an auxiliary support. There are defects such as complicated surgical procedure, high surgical cost, high patient trauma, high risk of complications, long hospital stay, painful recovery process and the like.

SUMMARY

The technical problem to be solved by the present disclosure is to provide a heart valve repair method rooting for the above-mentioned defects in the prior art. At least one suture is firstly implanted in each leaflet of the mitral or tricuspid valve. The multiple sutures are then fixed together to pull the leaflets of the mitral or tricuspid valve toward each other, reducing or eliminating the gap between the mitral or tricuspid valve, to treat the mitral regurgitation or the tricuspid regurgitation. The heart valve repair method of the present disclosure is particularly suitable for transapical minimally invasive surgery, which has simple surgical procedure, lower operation cost, lower patient trauma, lower risk of complications, and rapid recovery process.

The technical solution adopted by the present disclosure to solve its technical problems is:

A heart valve repair method, applied to a heart valve repair system, the heart valve repair system comprising a plurality of sutures and a suture implanting apparatus; the heart valve repair method comprising:

advancing a distal end of the suture implanting apparatus from an outside of a body through a transapical approach into a left ventricle or a right ventricle of a heart;

holding each leaflet of a heart valve with the distal end of the suture implanting apparatus, and implanting at least one suture into the leaflet; and withdrawing the distal end of the suture implanting apparatus from the body.

A heart valve repair method, applied to a heart valve repair system, the heart valve repair system comprising a plurality of sutures and a suture implanting apparatus, at least one end of each suture being provided with at least one fixing member respectively, the suture implanting apparatus comprising a capturing assembly, a puncturing assembly, and a pushing shaft, the pushing shaft axially defining a plurality of lumens, the puncturing assembly and the capturing assembly being movably received in different lumens of the pushing shaft, the capturing assembly comprising a capturing rod, a distal clamp and a proximal clamp, the plurality of sutures being received in the capturing rod and extending out from the distal clamp, the puncturing assembly comprising a puncturing needle and a puncturing rod coupled to a proximal end of the puncturing needle, the heart valve repair method comprising:

advancing a distal end of the suture implanting apparatus from an outside of a body through a transapical approach into a left ventricle or a right ventricle of a heart;

pushing the capturing rod to separate the distal clamp from the proximal clamp and holding each leaflet of a heart valve using the distal clamp and the proximal clamp;

pushing the puncturing rod to drive the puncturing needle to puncture the leaflet and couple to the corresponding fixing member of the suture after puncturing through the leaflet;

withdrawing the puncturing rod to drive the fixing member and the suture through the leaflet to implant the suture into the leaflet; and withdrawing the distal end of the suture implanting apparatus from the body.

A heart valve repair method, applied to a heart valve repair system, the heart valve repair system comprising a plurality of sutures, a suture implanting apparatus, and a suture locking apparatus; the heart valve repair method comprising:

advancing a distal end of the suture implanting apparatus from an outside of a body through a transapical approach into a left ventricle or a right ventricle of a heart;

holding each leaflet of a heart valve with the distal end of the suture implanting apparatus, and implanting at least one suture into the leaflet;

withdrawing the distal end of the suture implanting apparatus from the body;

advancing a distal end of the suture locking apparatus from the outside through the transapical approach into the corresponding left ventricle or the corresponding right ventricle;

using the distal end of the suture locking apparatus to lock the plurality of sutures in the corresponding left ventricle or the corresponding right ventricle; and withdrawing the distal end of the suture locking apparatus from the body.

A heart valve repair method, applied to a heart valve repair system, the heart valve repair system comprising a plurality of sutures, a suture implanting apparatus and a suture locking apparatus, at least one end of the suture being provided with at least one fixing member respectively, the suture implanting apparatus comprising a capturing assembly, a puncturing assembly, and a pushing shaft, the pushing shaft axially defining a plurality of lumens, the puncturing assembly and the capturing assembly being movably received in different lumens of the pushing shaft, the capturing assembly comprising a capturing rod, a distal clamp and a proximal clamp, the plurality of sutures being received in the capturing rod and extending out from the distal clamp, the puncturing assembly comprising a puncturing needle and a puncturing rod coupled to a proximal end of the puncturing needle, the heart valve repair method comprising:

advancing a distal end of the suture implanting apparatus from an outside of a body through a transapical approach into a left ventricle or a right ventricle of a heart;

pushing the capturing rod to separate the distal clamp from the proximal clamp and holding each leaflet of a heart valve using the distal clamp and the proximal clamp;

pushing the puncturing rod to drive the puncturing needle to puncture the leaflet and couple to the corresponding fixing member of the suture after puncturing through the leaflet;

withdrawing the puncturing rod to drive the fixing member and the suture through the leaflet to implant the suture into the leaflet;

withdrawing the distal end of the suture implanting apparatus from the body;

advancing a distal end of the suture locking apparatus from the outside of the body through the transapical approach into the corresponding left ventricle or the corresponding right ventricle;

using the distal end of the suture locking apparatus to lock the plurality of sutures in the corresponding left ventricle or the corresponding right ventricle; and withdrawing the distal end of the suture locking apparatus from the body.

Compared with the prior art, the heart valve repair method of the present disclosure has at least the following beneficial effects:

The heart valve repair method of the present disclosure is suitable for a valve repair surgery of mitral regurgitation or tricuspid regurgitation by transapical treatment, and can quickly realize a chordae repair or an edge-to-edge repair of the mitral valve or the tricuspid valve. When using, it is only necessary to form a small incision with a diameter ranging from 1 cm to 5 cm in a chest of a patient. After a transapical puncture, a suture is implanted into a leaflet, and then an end of the suture can be fixed on a ventricular wall or a papillary muscle, and the suture is used as an artificial chordae to achieve "chordae repair"; or use the suture locking apparatus to fix the multiple sutures on the different leaflets together, thereby pulling the leaflets of the mitral or tricuspid valve toward each other, reducing or eliminating the gap between the leaflets, so as to achieve "edge-to-edge repair".

Therefore, the heart valve repair method of the present disclosure can treat the organic regurgitation and functional regurgitation of the mitral or tricuspid valve, and the whole surgical procedure only forms a small wound on the chest of the patient, which is minimally invasive and avoids a damage of a tradition thoracotomy to the patient. The instrument is easy to operate, avoiding tedious steps of the prior art of a transcatheter repair of the mitral or tricuspid valve, the success rate of the operation is high, and the time is short.

In addition, the operator can adjust the gap between the leaflets of the mitral or tricuspid valve before using the suture locking apparatus to fix the sutures, and observe the regurgitation through a medical imaging device. In the case of adjustment to the state of mitral regurgitation or tricuspid regurgitation in the slightest or complete elimination, the lock pin can fix the sutures, thereby ensuring the surgical effect and improving the success rate of the operation.

BRIEF DESCRIPTION OF THE ACCOMPANYING DRAWINGS

To describe the technology solutions in the embodiments of the present disclosure more clearly, the following briefly introduces the accompanying drawings required for describing the embodiments. Obviously, the accompanying drawings in the following description show merely some embodiments of the present disclosure, those of ordinary skill in the art may also derive other obvious variations based on these accompanying drawings without creative efforts.

FIG. 10a is a structural schematic diagram showing a structure of a proximal clamp in the suture implanting apparatus of FIG. 6.

FIG. 10b is a cross-sectional view taken along line B-B of FIG. 10a.

FIGS. 14a-14g are structural schematic diagrams of the gripping auxiliary assembly in different embodiments.

FIG. 20 is a schematic view of the detecting process of the detecting assembly of FIG. 19a.

FIG. 32a and FIG. 32b are partial enlarged views of a portion b of FIG. 31a and

FIG. 31b at C.

FIGS. 33 to 45 are schematic views showing a process of repairing a mitral valve using the heart valve repair system provided by the present disclosure.

Figure 46:
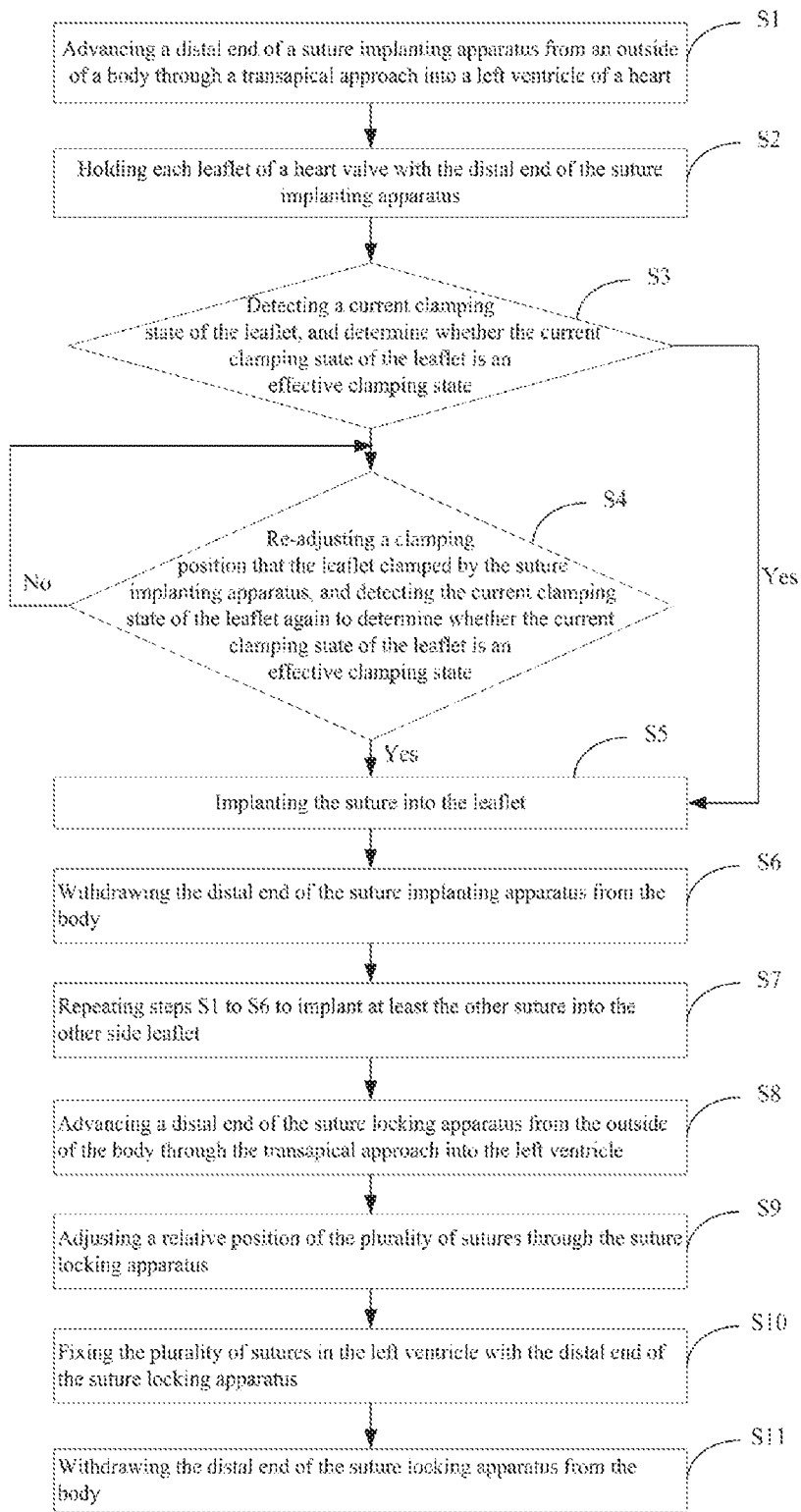

FIG. 46 is a schematic flow chart of a heart valve repair method provided by the present disclosure for repairing a mitral valve.

DETAILED DESCRIPTION OF ILLUSTRATED EMBODIMENTS

The technical solution in the embodiments of the present disclosure will be described clearly and completely hereinafter with reference to the accompanying drawings in the embodiments of the present disclosure. Obviously, the described embodiments are merely some but not all embodiments of the present disclosure. All other embodiments obtained by a person of ordinary skilled in the art based on the embodiments of the present disclosure without creative efforts shall fall within the protection scope of the present disclosure.

Orientation definition: an orientation close to an operator is defined as a proximal/proximal end, and another orientation away from the operator is defined as a distal/distal end.

Figures 1A, 1B:
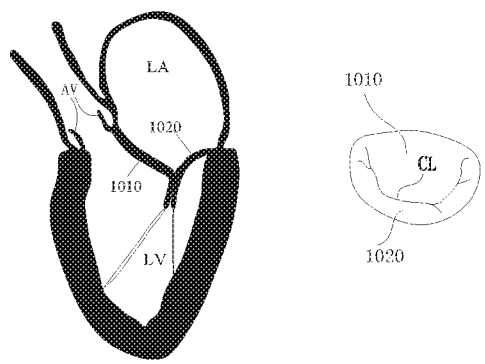
FIGS. 1a to 1b are schematic diagrams of a normally closed mitral valve in a heart.
Figures 2A, 2B:
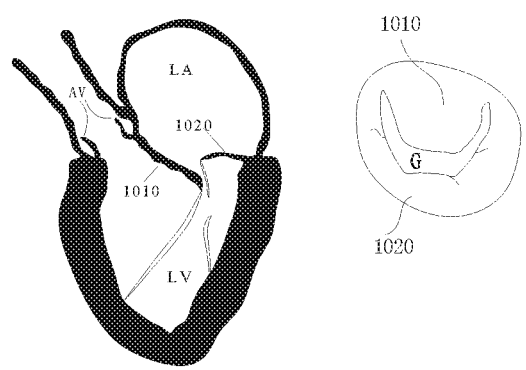
FIGS. 2a to 2b are schematic diagrams of a mitral valve that does not normally close in the heart.
Figure 3:
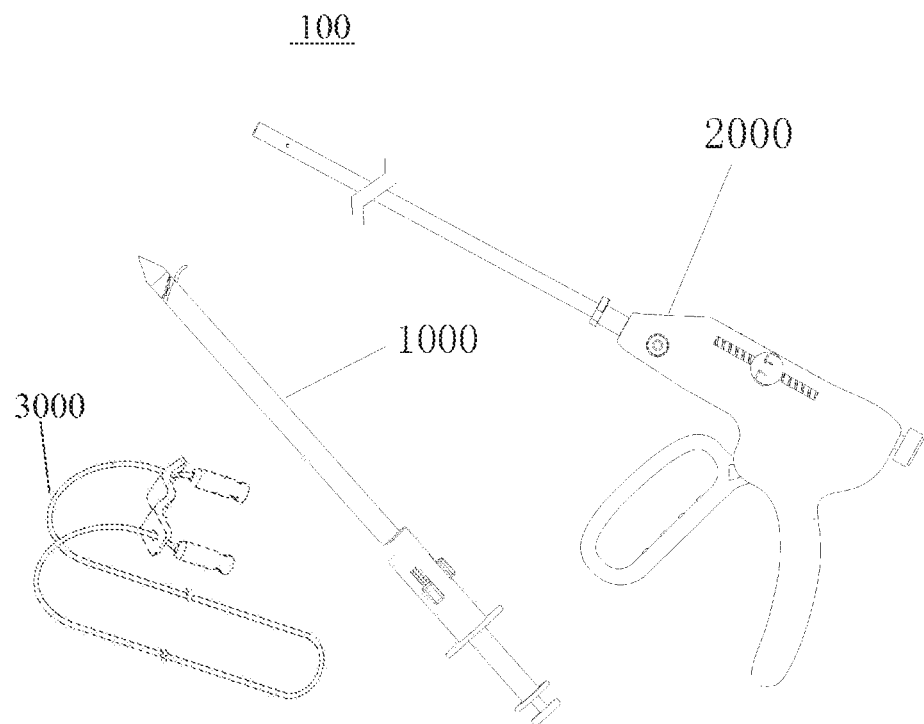
FIG. 3 is a structural schematic diagram of a heart valve repair system of the present disclosure.

As shown in FIG. 3, a heart valve repair system 100 provided by the present disclosure can include at least two sutures 3000 each having a certain axial length, a suture implanting apparatus 1000 for implanting the at least two sutures 3000 in different leaflets of a heart valve respectively, and a suture locking apparatus 2000 for fixing the at least two sutures 3000 together.

Figure 7:
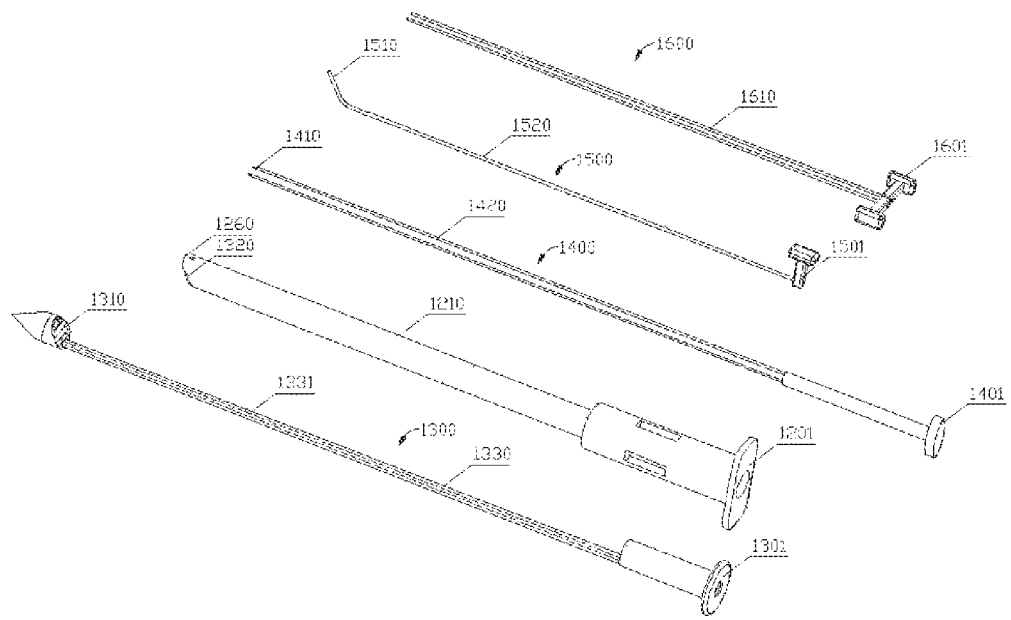
FIG. 7 is an exploded view of the suture implanting apparatus of FIG. 6.

As shown in FIG. 7, the suture implanting apparatus 1000 can include a pushing shaft 1210, a capturing assembly 1300 for capturing and holding the leaflets, and a puncturing assembly 1400 for puncturing the leaflets. The capturing assembly 1300 and the puncturing assembly 1400 can be movably received in the pushing shaft 1210. The suture 3000 can be received in the capturing assembly 1300.

Figure 4:
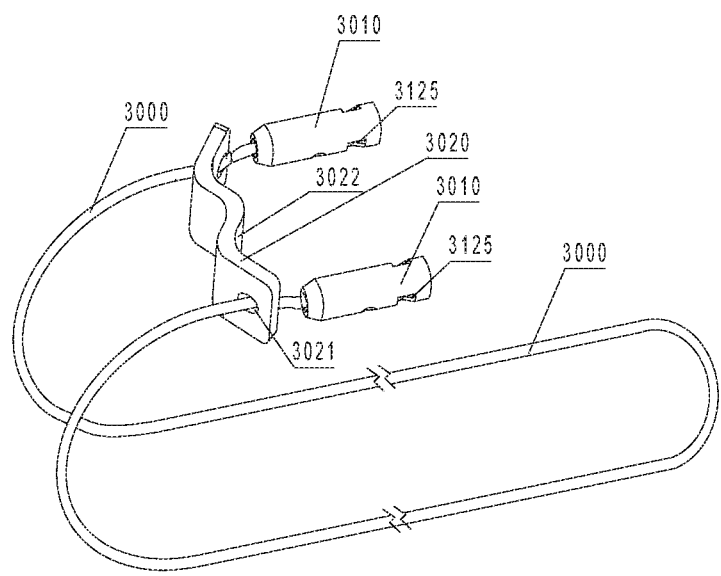
FIG. 4 is a structural schematic diagram of a suture of FIG. 3.

As shown in FIGS. 4, and 5a-5c, in this embodiment, the heart valve repair system 100 can include at least two sutures 3000. Each suture 3000 has a certain axial length, and is flexible. At least one of two ends of the suture 3000 each is coupled to one fixing member 3010. The fixing member 3010 is coupled to the puncturing assembly 1400 through a non-detachable or a detachable fixed connection. In this embodiment, the suture 3000 is preferably provided with two fixing members 3010 at two ends thereof respectively (as shown in FIG. 4).

In the multiple sutures 3000, one part of each suture 3000 is fixed in the leaflet. All sutures 3000 are secured together by the suture locking apparatus 2000 to pull the multiple leaflets of the heart valve toward each other. The sutures 3000 having flexibility means that they cannot stretched in the axial direction thereof and bend freely. The suture 3000 can be made of biocompatible polymer materials or relatively soft metal materials, and is preferably polymer materials such as PTFE or PP. In this embodiment, an ePTFE material is used.

In at least one embodiment, one end of each suture 3000 is fixed on the leaflet and the other end of each suture 3000 can be secured to a ventricular wall or a papillary muscle. Therefore, the suture 3000 can be used as an artificial chordae for replacing a decreased chordae, so as to improve the mitral regurgitation due to chordae rupture and the like.

Figure 5A:
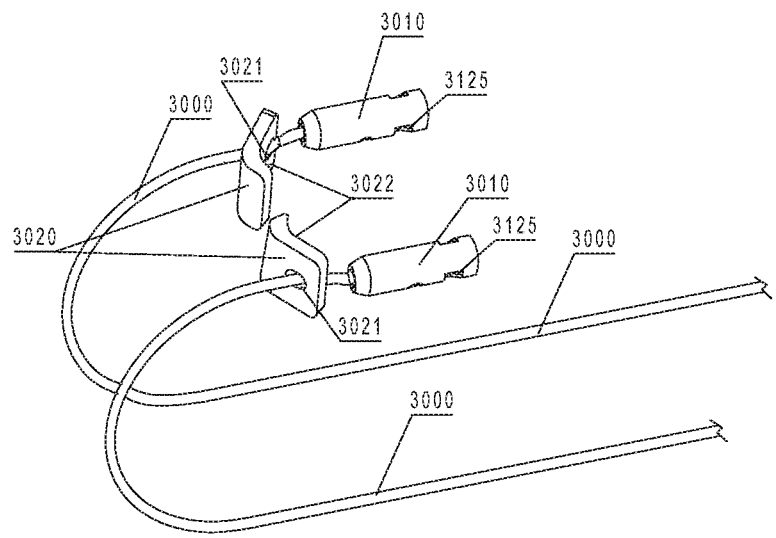
FIGS. 5a to 5c are structural schematic diagrams of the suture in different embodiments.
Figure 5B:
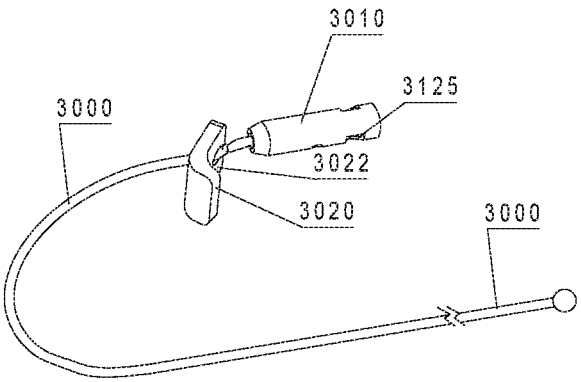
Figure 5C:
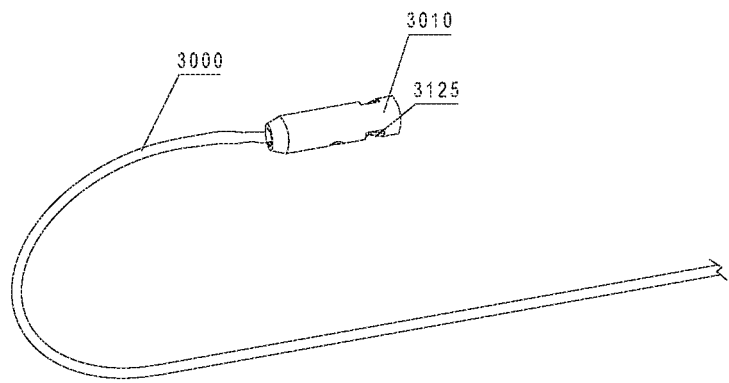

As shown in FIG. 4, two fixing members 3010 are coupled with two ends of the suture 3000 respectively. Also, as shown in FIGS. 5a-5c, only one fixing member 3010 is coupled to one end of the suture 3000. Each time the operator operates the suture implanting apparatus 1000, two or more sutures 3000 can be implanted, or only one suture 3000 can be implanted at a time. The suture 3000 is fixed to the fixing member 3010. The fixing ways can be but are not limited to knotting, winding, welding, bonding, snapping, and the like. For example, after one end of the suture 3000 passes through the fixing member 3010, the end of the suture 3000 is knotted to form a larger diameter coil. Or, the end of the suture 3000 is welded to form a larger diameter ball. Or, the end of the suture 3000 is provided with a cross positioning rod. When only one end of the suture 3000 is provided with one fixing member 3010, as other end of the suture 3000 is not provided with one fixing member 3010, therefore, as shown in FIG. 5b, the diameter of the other end should be larger than the diameter of the suture 3000 by knotting, winding, setting a spherical end, setting a disc end, or the like. When the suture 3000 is implanting into the leaflet, one end of the suture 3000 is coupled with the puncturing assembly 1400 through the fixing member 3010, and is then withdrawn, and the other end of the suture 3000 having a larger diameter is fixed on an upper surface of the leaflet.

In order to increase a point contact between the suture line 3000 and the leaflet to a surface contact, thereby reducing a risk of the suture 3000 tearing the leaflet, the suture 3000 is preferably sleeved with an anti-slip member 3020, and the anti-slip member 3020 can slide along an axial direction of the suture 3000. Since the anti-slip member 3020 is previously sleeved on the suture 3000, after a puncturing needle 1410 of the suture implanting device 1000 punctures the leaflet and is coupled with the fixing member 3010 located at an end of the suture 3000, the anti-slip member 3020 can be driven to a puncturing point, and is fixed to the leaflet together with the suture 3000. The anti-slip member 3020 defines at least one through hole 3021. The at least one suture 3000 passes through the at least one through hole 3021. The number of the at least one through hole 3021 is related to the fixing way of the anti-slip member 3020. One way is that the anti-slip member 3020 defines at least two through holes 3021, two ends of one suture 3000 pass through two different through holes 3021 respectively, and are then coupled to one fixing member 3010 (as shown in FIG. 4). Another way is that each anti-slip member 3020 defines one through hole 3021, one end of the suture 3000 passes through the through hole 3021 and is then coupled to the fixing member 3010 (as shown in FIGS. 5a and 5b). In order to prevent the anti-slip member 3020 from slipping off the suture 3000, the diameter of the through hole 3021 is less than the diameter of the fixing member 3010, and another end of the suture 3000 having no fixing member 3010 should have a diameter greater than a diameter of the through hole 3021 of the anti-slip member 3020 by a way of knotting, setting the spherical end, setting the disc end, or the like (as shown in FIG. 5b).

In order to spread the force of the suture 3000 to the leaflet as far as possible to a contact surface between the anti-slip member 3020 and the leaflet, the anti-slip member 3020 needs to be in contact with the leaflet as much as possible, so the anti-slip member 3020 is provided with a contact surface 3022 that is in contact with the leaflet. Except for the contact surface 3022, the specific structure of the anti-slip member 3020 is not limited, and may be a sheet shape, a disk shape or a spherical shape, or even an irregular shape having a certain area, and is preferably a sheet shape. The anti-slip member 3020 may be a non-porous structure, a mesh structure, a bar-like structure, or the like. The anti-slip member 3020 should be made of biocompatible materials, either of elastic materials or non-elastic materials. Specifically, the anti-slip member 3020 is selected from at least one of an elastic pledget, a heart patch, a felt sheet, a mesh structure, a disc-like structure, or a double disc-like structure. The structure of the anti-slip member 3020 having the disk-like structure or the double-disc structure is similar to an occluder in the prior art, and will not be described herein. Preferably, in order to reduce an overall size of the suture implanting apparatus 1000, the anti-slip member 3020 having the disc-like structure or the double disc-like structure should be made of shape memory materials. In this embodiment, a polyester cloth gasket is used as the anti-slip member 3020.

Figure 6:
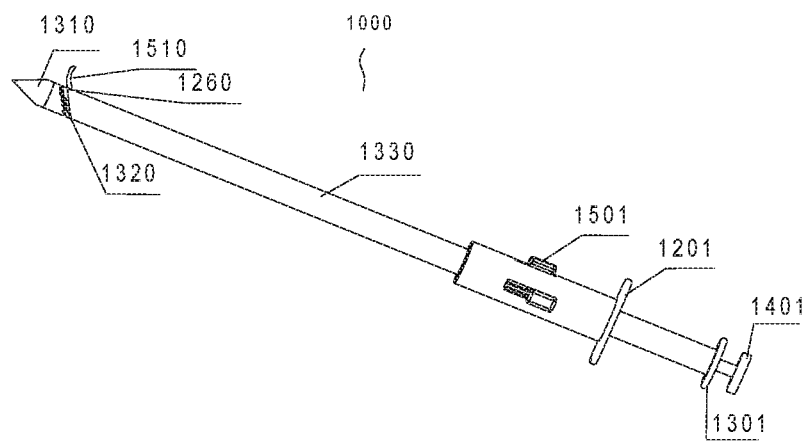
FIG. 6 is a structural schematic diagram showing a structure of a suture implanting apparatus of FIG. 3.
Figure 8:
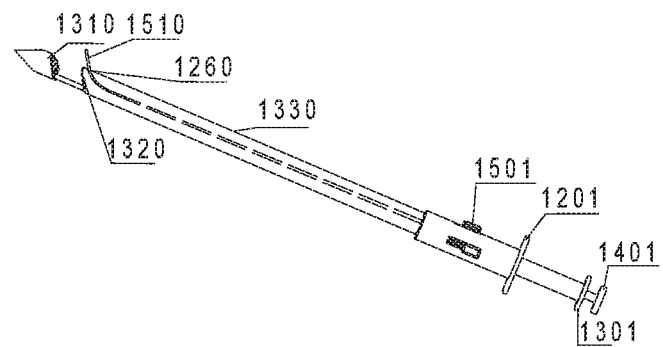
FIG. 8 is a structural schematic diagram showing a structure of the suture implanting apparatus of FIG. 6a when the capturing assembly in an open state.

The suture implanting apparatus 1000 is used for implanting at least one suture 3000 in each leaflet. As shown in FIGS. 6 to 8, the suture implanting apparatus 1000 can include a capturing assembly 1300, a puncturing assembly 1400 and a pushing shaft 1210. The pushing shaft 1210 is a tubular body having a certain axial length or a rod-shaped body having multiple lumens. The pushing shaft 1210 can be made of same materials and have multiple lumens. Alternatively, the pushing shaft 1210 can be a rod-shaped body formed by an outer tube and a plurality of inner tubes received and fixed in the outer tube. The pushing shaft 1210 can be made of biocompatible polymer materials (for example, polyformaldehyde, polyethylene, nylon, polyvinyl chloride, acrylonitrile butadiene styrene copolymers, thermoplastic elastomer Pebax or polyurethane), metal materials (for example, stainless steel or nickel-titanium alloy) or metal-polymer composite materials. In this embodiment, the pushing shaft 1210 is a rod-shaped body in which a plurality of mutually separated lumens are disposed in an axial direction thereof. A proximal end of the pushing shaft 1210 can include a first handle 1201. The first handle 1201 is used for pushing the pushing shaft 1210 towards the distal end or withdrawing the pushing shaft 1210 towards the proximal end.

As shown in FIG. 7 again, one lumen of the pushing shaft 1210 is used for movably receiving the puncturing assembly 1400. The puncturing assembly 1400 can include at least one puncturing rod 1420 and at least one puncturing needle 1410 each located on a distal end of one of the at least one puncturing rod 1420. The number of the at least one puncturing rod 1420 is related to the number of the fixing members 3010. In this embodiment, as shown in FIG. 4, two ends of the suture 3000 are coupled with the two fixing members 3010 respectively, therefore, there are two puncturing rods 1420 parallel receiving in the pushing shaft 1210. Each puncturing needle 1410 is corresponded to one fixing member 3010. The puncturing needle 1410 punctures the leaflet and then couples with the fixing member 3010 of the suture 3000. Then, the puncturing rod 1420 is withdrawn to drag the suture 3000 to the proximal end. The distal end of the puncturing needle 1410 is a straight tip having a tapered shape to facilitate a puncture of the leaflet and reduce a diameter of the puncturing point formed on the leaflet, thereby facilitating postoperative healing of the patient. In this embodiment, a diameter of a single puncturing point formed on each leaflet formed by the suture implanting apparatus 1000 has a range from 0.3 mm to 1.5 mm. Furthermore, by selecting a suitable shape and a diameter of the puncturing needle 1410, the diameter of the puncturing point can be controlled to be about 0.7 mm.

Figure 9:
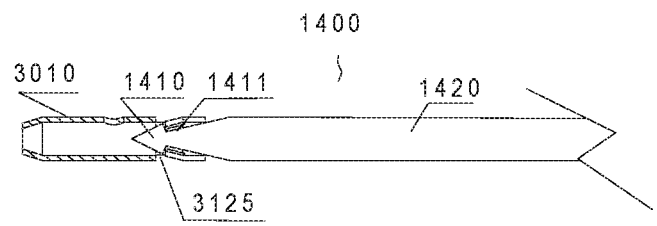
FIG. 9 is a structural schematic diagram showing a structure of a puncturing needle of a puncturing assembly coupling with a fixing member of the suture in the suture implanting apparatus of FIG. 6.

The puncturing needle 1410 is coupled to the fixing member 3010 through a non-detachable or a detachable fixed connection way. The connection way is various, for example, screw connection, bonding, frictional connection through rough surface, interference fit or snap connection. In this embodiment, the snap connection is used. Specifically, a groove or a hole is formed in an inner surface of the fixing member 3010, and is engaged with a protrusion or a convex edge provided by the puncturing needle 1410. As shown in FIG. 9, three recesses 3125 are radially defined on the inner surface of the fixing member 3010, and are engaged with the flanges 1411 on the puncturing needle 1410.

As shown in FIG. 7, a proximal end of the puncturing needle 1410 is coupled to the puncturing rod 1420. The puncturing rod 1420 is movably received in the lumen of the pushing shaft 1210. The proximal end of the puncturing rod 1420 extends out from the proximal end of the pushing shaft 1210 and then couples with a third handle 1401. Therefore, an axial movement of the third handle 1401 can cause the puncturing rod 1420 to move along an axial direction of the pushing shaft 1210, thereby driving the puncturing needle 1410 to puncture towards the distal end or withdraw towards the proximal end. After the leaflet is captured by the capturing assembly 1300, the puncturing needle 1410 can be driven by the third handle 1401 to puncture the leaflet and then couple with the fixing member 3010 of the suture 3000. In this embodiment, the puncturing needle 1410 forms a stable and reliable connection with the fixing member 3010 of the suture 3000, and the suture 3000 is not easily separated from the fixing member 3010, and the operator can conveniently and quickly withdraw one or both ends of the suture 3000 coupling with the fixing member 3010.

As shown in FIGS. 6 to 8, the capturing assembly 1300 can include a capturing rod 1330 for receiving the suture 3000, and a distal clamp 1310 and a proximal clamp 1320. The distal clamp 1310 and the proximal clamp 1320 can open and close relatively to hold the leaflet. The capturing rod 1330 movably receives in the pushing shaft 1210. The distal clamp 1310 is located on the distal end of the capturing rod 1330. The proximal clamp 1320 is located on the distal end of the pushing shaft 1210. The proximal end of the capturing rod 1330 extends out from the proximal end of the pushing shaft 1210, and then couples with the a second handle 1301. The distal clamp 1310 and the proximal clamp 1320 can open and close relatively means that the distal clamp 1310 and the proximal clamp 1320 can move relative to each other to open or close. The second handle 1301 is driven to the distal end, causing the capturing rod 1330 to move toward the distal end, so that the distal clamp 1310 is away from the proximal clamp 1320, forming an open state as shown in FIG. 8. At this time, the distal clamp 1310 and the proximal clamp 1320 can cooperatively form a receiving space for receiving the leaflet. When the leaflet is received in the receiving space, the second handle 1301 is withdrawn to the proximal end, such that the distal clamp 1310 moves close to the proximal clamp 1320, forming a close state as shown in FIG. 6. At this time, the leaflet is captured by the capturing assembly 1300 and fixed. The shape of the proximal clamp 1320 and the distal clamp 1310 should be consistent with the shape of the pushing shaft 1210. The distal clamp 1310 and the proximal clamp 1320 should form a smooth overall appearance after they are in the close state to facilitate pushing and reducing damage to the patient's wound.

In at least one embodiment, the proximal clamp 1320 set separately can be omitted, and the distal end of the pushing shaft 1210 can be directly used as the proximal clamp 1320 to cooperate with the distal clamp 1310 to hold the leaflet.

In order to improve the stability of the clamping, a clamping surface of the proximal clamp 1320 (ie, a distal end surface of the proximal clamp 1320) and a clamping surface of the distal clamp 1310 (ie, a proximal end surface of the distal clamp 1310) should be fitted with each other for clamping the leaflet. The clamping surface of the proximal clamp 1320 and the clamping surface of the distal clamp 1310 each has a larger leaflet contact area. For example, the clamping surface of the proximal clamp 1320 and the clamping surface of the distal clamp 1310 can be inclined respectively, that is, an acute angle of less than 90 degrees is formed between the axial direction of the pushing shaft 1210 and the clamping surface of the proximal clamp 1320, and between the axial direction of the pushing shaft 1210 and the clamping surface of the distal clamp 1310. Furthermore, a clamping reinforcement for enhancing the clamping force is provided on the clamping surface of the distal clamp 1310 and/or the proximal clamp 1320. The clamping reinforcement is preferably at least one of projections, ribs, grooves or recesses. The clamping surface of the distal clamp 1310 is provided with a clamping reinforcement that should be matched to a clamping reinforcement provided by the clamping surface of the proximal clamp 1320, such that there is no gap between the distal clamp 1310 and the proximal clamp 1320 when they are in the close state. In this embodiment, the clamping surface of the distal clamp 1310 and the clamping surface of the proximal clamp 1320 should both provided with clamping reinforcement having a plurality of parallel ribs, when the distal clamp 1310 and the proximal clamp 1320 are in the close state, there is no gap between the distal clamp 1310 and the proximal clamp 1320.

Figures 10A, 10B:
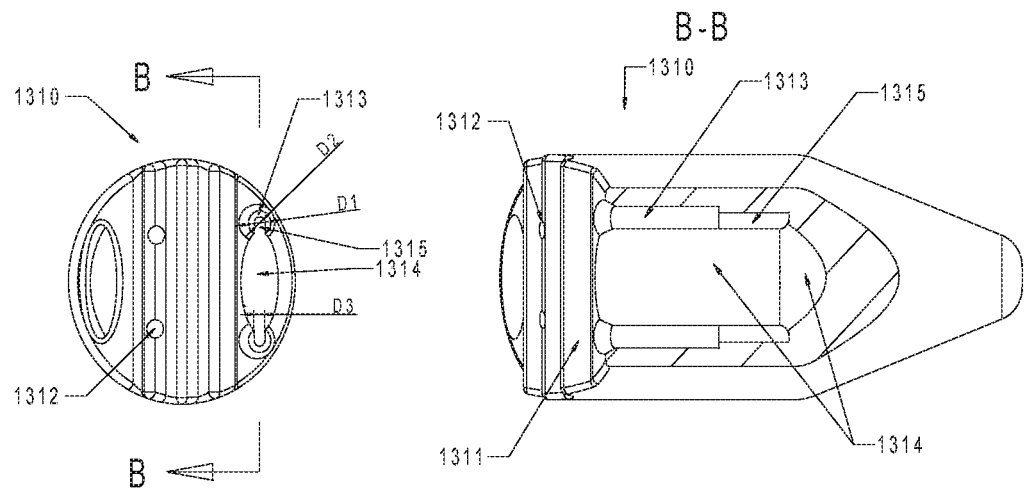

The capturing rod 1330 is a tubular body or a hollow rod having a certain axial length. Referring to FIG. 10a and FIG. 10b together, a cross section of the capturing rod 1330 is preferably elliptical, semicircular, crescent, circular, or the like. The capturing rod 1330 defines a suture channel 1331 (as shown in FIG. 7) along an axial direction thereof. The distal clamp 1310 defines two suture receiving spaces 1315 interconnecting with the suture channel 1331. The two suture receiving spaces 1315 are respectively drilling through the clamping surfaces of the distal clamp 1310. The suture 3000 is received in the suture channel 1331 and the two suture receiving spaces 1315.

The clamping surface of the distal clamp 1310 defines two fixed cavities 1313 for accommodating the two fixing members 3010 of the suture 3000, respectively. Each fixed cavity 1313 is axially interconnected with one suture receiving cavity 1315. The positions of the two fixed cavities 1313 correspond to the positions of the two puncturing needles 1410, respectively. Thus, the two fixing members 3010 of the suture 3000 are respectively accommodated in the distal clamp 1310. The proximal end of each fixing member 3010 corresponds to one puncturing needle 1410.

In this embodiment, the suture 3000 is placed and fixed inside the suture implanting apparatus 1000, which avoids the damage of the friction of the suture 3000 when the suture 3000 enters the patient body following the suture implanting apparatus 1000, and further avoids leakage of blood around the suture 3000. In addition, the distance between the fixed cavity 1313 and the capturing rod 1330 is the distance between the implanted suture 3000 and the edge of the leaflet, which can effectively avoid the edge of the leaflet folding or a notch of the mitral valve, to enhance the surgical effect.

As shown in FIGS. 10a-10b, since the suture 3000 is further provided with the anti-slip member 3020 sleeved thereon, the clamping surface of the distal clamp 1310 further defines a receiving groove 1314 for receiving the anti-slip member 3020. The receiving groove 1314 is radially interconnected with two suture receiving cavities 1315. Therefore, after the two puncturing needle 1410 each punctures the leaflet and couples with one fixing member 3010, the two puncturing rods 1420 are withdrawn to pull out the two puncturing needles 1410, the two fixing members 3010, the sutures 3000, and the two anti-slip members 3020 sequentially from the clamping surface of the distal clamp 1310, until the two puncturing needles 1410, the two fixing members 3010 and the sutures 3000 drill through the leaflet in turn, and the anti-slip member 3020 is attached to the upper surface of the leaflet.

The fixed cavity 1313 and the receiving groove 1314 can be used to pull the suture 3000 and the anti-slip member 3020 to the leaflet without releasing the distal clamp 1310 and the proximal clamp 1320. Therefore, when the distal clamp 1310 and the proximal clamp 1320 are changed from the close state to the open state, and the leaflet is in the moment of detachment from the capturing assembly 1300 and recovery beating, the suture 3000 will not be in contact with the leaflet alone, avoiding a linear cutting effect of the suture 3000 from injuring the beating leaflet.

The function of the fixed cavity 1313 is that the fixing member 3010 of the suture 3000 can be fixed in the fixed cavity 1313, and the fixing member 3010 can be pulled out from the fixed cavity 1313 after being pulled by an external force. Therefore, the shape of the fixed cavity 1313 matches the shape of the fixing member 3010, and a diameter of an inscribed circle of the fixed cavity 1313 is larger than a diameter of a circumscribed circle of the suture receiving cavity 1315. Preferably, a ratio of the diameter of the circumscribed circle of the suture receiving cavity 1315 to the diameter of the inscribed circle of the fixed cavity 1313 is (0.2 to 0.4):1. When a cross section of the fixed cavity 1313 and the suture receiving cavity 1315 are both circular, the diameter of the inscribed circle of the fixed cavity 1313 is the diameter of the circular cross section of the fixed cavity 1313, and the diameter of the circumscribed circle of the suture receiving cavity 1315 is the diameter of the circular cross section of the suture receiving cavity 1315. In this embodiment, the cross section of the fixed cavity 1313 is circular, and the diameter of the fixed cavity 1313 is D1. The cross section of the suture receiving cavity 1315 is circular, and the diameter of the suture receiving cavity 1315 is D2. D2 is 30% of D1.

In order to smoothly pull the suture 3000 and the anti-slip member 3020 out of the clamping surface of the distal clamp 1310, the fixed cavity 1313 and the receiving groove 1314 are radially interconnected with each other. Preferably, the width D3 of the connecting portion between the fixed cavity 1313 and the receiving groove 1314 is 20% to 50% of D1.

Figures 11A, 11B:
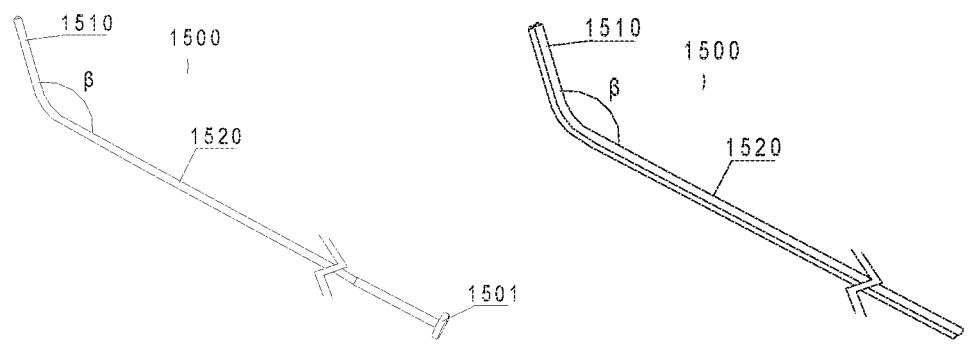
FIGS. 11a-11b are structural schematic diagrams of a gripping auxiliary assembly of the suture implanting apparatus of FIG. 6 in different embodiments.

As shown in FIG. 7, to further enhance the grip, the suture implanting apparatus 1000 can also include a gripping auxiliary assembly 1500. As shown in FIG. 11a and FIG. 11b, the gripping auxiliary assembly 1500 can include at least one gripping arm 1520 that is movably received into the pushing shaft 1210, and the at least one gripping member 1510 each is located at a distal end of one of the at least one gripping arm 1520. In order to facilitate the pushing, the gripping arm 1520 is also provided with a fourth handle 1501 at a proximal end thereof.

Figure 12:
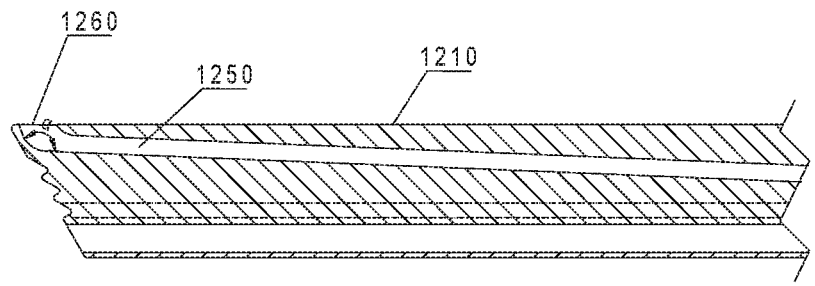
FIG. 12 is an axial cross-sectional view of a distal end of a pushing shaft of the suture implanting apparatus of FIG. 6.
Figures 13A, 13B:
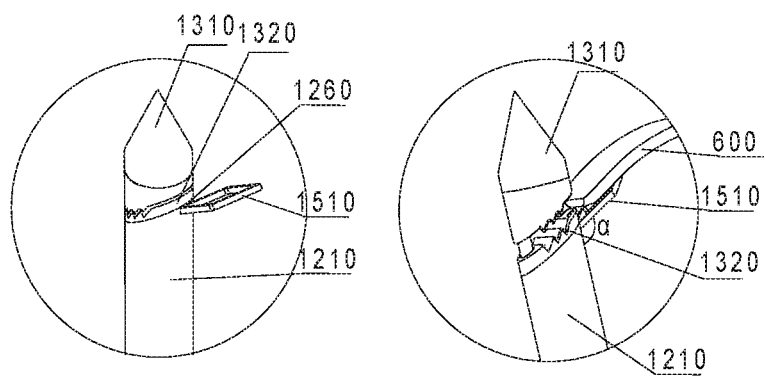
FIGS. 13a and 13b are structural schematic diagrams showing the gripping auxiliary assembly supporting on a lower surface of a leaflet.

As shown in FIG. 12, the pushing shaft 1210 defines a gripping arm receiving space 1250 along an axial direction thereof. Before puncturing, the gripping member 1510 and the gripping arm 1520 are both received in the gripping arm receiving space 1250. The clamping surface of the proximal clamp 1320, the sidewall of the pushing shaft 1210 or the sidewall of the proximal clamp 1320 defines an opening 1260. The opening 1260 is interconnected with the gripping arm receiving space 1250. When a fourth handle 1501 is pushed by an operator towards the distal end, the gripping arm 1520 can be driven to push the gripping member 1510 out from the opening 1260 (as shown in FIG. 13a), thereby supporting on a lower surface of the leaflet 600, steadying the beating leaflet 600, reducing an amplitude of the leaflet 600, and cooperating with the capturing assembly 1300 to clamp and fix the leaflet 600 (as shown in FIG. 13b)

The angle α between the axial direction of the distal end of the gripping arm receiving space 1250 and the axial direction of the pushing shaft 1210 ranges from 120 degrees to 150 degrees. The reason for setting this is that before puncturing, the capturing rod 1330 is in contact with the edge of the leaflet, and the distal clamp 1310 and the proximal clamp 1320 can only clamp part of the leaflet. In this case, in order to keep the beating leaflet stable and easy to puncture, it is necessary to be support other side opposite to the edge of each leaflet, so it is necessary to have a certain angle between the gripping member 1510 after drilling through the opening 1260 and the pushing shaft 1210, so as to support the lower surface of the other side of each leaflet opposite to the edge of the leaflet. The angle between the auxiliary member 1510 and the pushing shaft 1210 is approximately equal to the angle between the axial direction of the distal end of the gripping arm receiving space 1250 and the axial direction of the pushing shaft 1210.

The gripping member 1510 is a rod-like structure composed of at least one support rod. The gripping member 1510 is made of biocompatible elastic and/or flexible materials to accommodate the leaflet's anatomy and leaflet activity and avoid damage to the leaflet. The elastic materials are preferably shape memory materials. The gripping member 1510 can be made of metallic materials, polymeric materials or metal-polymer composite materials. The support rod may be a solid or hollow structure of a single layer or a multiple layer composite structure, or may be coiled from a single wire or a plurality of wires. In this embodiment, the gripping member 1510 is a support rod made of nickel-titanium alloy and has a circular cross section.

The gripping arm 1520 is rod-shaped or tubular with a certain axial length and has a certain hardness or rigidity to provide support and push ability. The gripping arm 1520 may be a metal rod or a polymer rod of a hollow or solid structure of a single layer or a multiple layer composite structure, or may be coiled from a single wire or a plurality of wires. The gripping arm 1520 can be made of metal materials, polymer materials or metal-polymer composite materials.

The supportability of the gripping arm 1520 and the softness of the gripping member 1510 can be achieved by using different materials to make the gripping member 1510 and the gripping arm 1520, respectively. It can be understood that the same materials can be used to make the gripping arm 1520 and the gripping member 1510, and then a higher hardness material is added outside or inside the gripping arm 1520 as a reinforcing tube or a stiffened wire to ensure the supportability of the gripping arm 1520 (as shown in FIG. 14a). Preferably, the gripping arm 1520 and the gripping member 1510 have an included angle (3 ranging from 120 degrees to 150 degrees.

The gripping member 1510 is at least partially made of radiopaque materials. After the gripping member 1510 is in contact with the leaflet, the flexible and/or elastic gripping member 1510 produces a corresponding swing with an amplitude of the leaflet's movement, so that the operator can quickly and accurately determine the position of the leaflet by X-ray before the clamping assembly 1300 holds the leaflet. Therefore, the capturing assembly 1300 can be operated to capture the leaflet more quickly and accurately, the operation cost and difficulty are reduced, the operation time is shortened, and the success rate of the operation is improved.

In at least one embodiment, in order to enhance the strength of the gripping auxiliary assembly 1500, the gripping member 1510 may also be a deformed structure composed of a plurality of support rods. After the deformed structure is contracted and deformed, it is received in the pushing shaft 1210 together with the gripping arm 1520. As shown in FIG. 14b, the deformed structure is an open bifurcated structure or an umbrella-like structure composed of a plurality of support rods, and an angle φ between the bifurcated structures is less than or equal to 150 degrees. In order to facilitate pushing in the pushing shaft 1210, the gripping member 1510 has a compressed state and an expanded state in a natural state. When the clamping auxiliary member 1510 is in the compressed state, it can be accommodated in the gripping arm receiving space 1250 of the pushing shaft 1210 and pushed. When the gripping member 1510 is extended out from the opening 1260, it is transformed into the expanded state, which can be supported on the lower surface of the leaflet, and stably beats of the leaflet. The contact surface of the larger diameter of the gripping member 1510 and the leaflet is the plane where the gripping member 1510 is located. Therefore, the contact area between the gripping member 1510 and the leaflet is larger, which can better fit the leaflet and improve the supportability for leaflets of the gripping auxiliary assembly 1500.

In at least one embodiment, the ends of the open bifurcated structure or the umbrella-like structure of the gripping member 1510 may be rolled in the direction towards the proximal end of the gripping arm 1520. The plurality of gripping members 1510 form a recessed area, as shown in FIG. 14c. At this time, since the end of each gripping member 1510 is turned inward and pointed to the direction of the proximal end of the gripping arm 1520. The end of the support rod of the gripping member 1510 can be prevented from stabbing the leaflet or the ventricular wall.

As shown in FIGS. 14d to 14f, in at least one embodiment, the deformed structure may also be a closed loop structure composed of a plurality of support rods. The closed loop structure may be circular, diamond, elliptical, pear-shaped, polygonal or other irregular shapes that may form a closed structure. Referring to FIG. 14g, in at least one embodiment, at least one flexible and/or elastic link rod 1511 may be disposed between the support rods of the closed-loop structure to improve the stability of the closed-loop structure, and further enhance the supportability of the gripping member 1510 to the leaflet. In at least one embodiment, when a plurality of support rods and link rods 1511 are disposed in the closed loop structure, the closed loop structure may also form a sheet structure or a mesh structure. As long as the gripping member 1510 is made of shape memory materials, it can be stored in the gripping arm receiving space 1250 of the pushing shaft 1210 and delivered, and then extended out from the opening 1260 to return to a natural unfolded state, contact with the lower surface of the leaflet and provide support for the leaflet.

Figure 15:
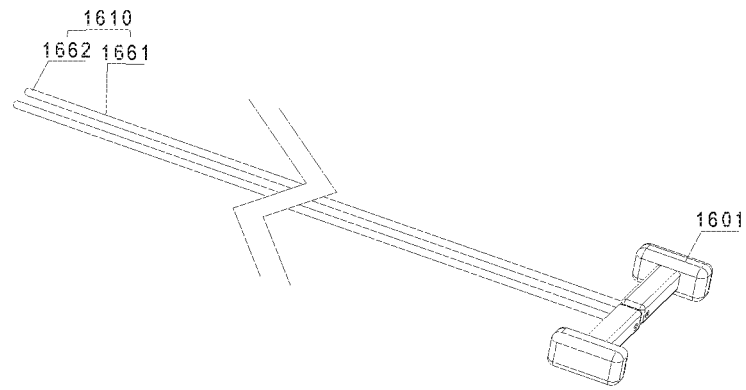
FIG. 15 is a structural schematic diagram showing a detecting assembly in the suture implanting apparatus of FIG. 6.

As shown in FIG. 7 again, the suture implanting apparatus 1000 can further include a detecting assembly 1600. The detecting assembly 1600 is used to detect whether the leaflet is effectively clamped between the distal clamp 1310 and the proximal clamp 1320. The detecting assembly 1600 can include at least one probe 1610. As shown in FIG. 15, in this embodiment, the detecting assembly 1600 can include two probes 1610 arranged in parallel. The distance between the two probes 1610 and the capturing rod 1330 is approximately equal.

Figure 16:
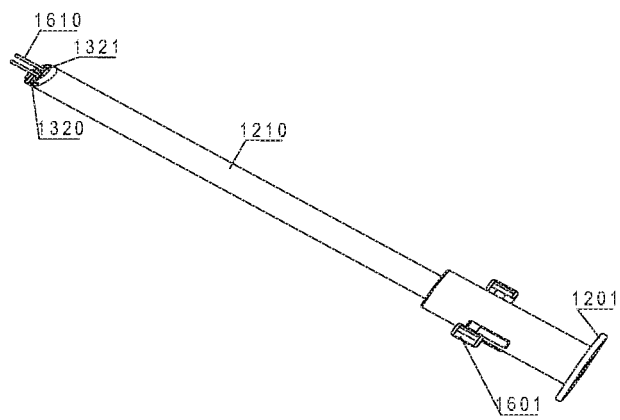
FIG. 16 is a structural schematic diagram showing the detecting assembly of FIG. 15 drilled through the pushing shaft.
Figure 17:
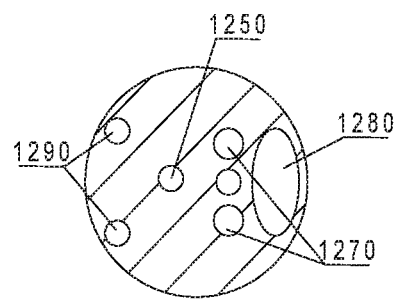
FIG. 17 is a radial cross-sectional view of the pushing shaft.

As shown in FIGS. 16 and 17, to ensure that the probe 1610 can protrude from the distal end of the pushing shaft 1210 to detect the leaflet, an axial length of the probe 1610 is preferably greater than a minimum length of the pushing shaft 1210 along the axial direction thereof. In the pushing shaft 1210, at least one probe channel 1270, a capturing rod channel 1280, and at least one puncturing rod channel 1290 are disposed in the axial direction. The probe 1610 movably drills through the probe channel 1270 of the pushing shaft 1210. For ease of operation, the proximal end of each probe 1610 is coupled to one fifth handle 1601. The clamping surface of the proximal clamp 1320 defines at least one probe outlet 1321 for facilitating the distal end of the probe 1610 to extend therefrom. As shown in FIG. 10b, the clamping face of the corresponding distal clamp 1310 defines at least one probe receiving cavity 1312 each opposite to one probe outlet 1321 for receiving the distal end of the probe 1610. When the proximal clamp 1320 and the distal clamp 1310 are closed, the distal end of the probe 1610 is extended out from the probe outlet 1321 and then received in the probe receiving cavity 1312.

Figures 18A, 18B, 18C:
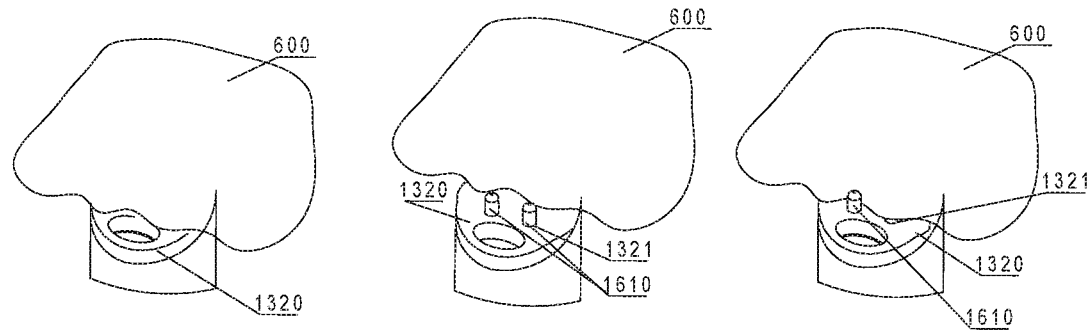
FIGS. 18a to 18c are schematic views of a detecting process of the detecting assembly.

As shown in FIG. 18a, when the proximal clamp 1320 and the distal clamp 1310 are in the close state, if the leaflet 600 is located between the proximal clamp 1320 and the distal clamp 1310, the edge of the leaflet 600 is in contact with the capturing rod 1330, after the distal end of the probe 1610 extends from the clamping surface of the proximal clamp 1320, the probe 1610 will be blocked by leaflet 600 and cannot move towards the distal end, it indicates that the leaflet 600 is in an effective clamping state and can be punctured. In addition, when the distal end of the probe 1610 is blocked by the leaflet 600 and cannot enter the probe receiving cavity 1312 shown in FIG. 10a, it also indicates that the position between the edge of the leaflet 600 and the suture 3000 is relatively fixed. As shown in FIG. 18b or FIG. 18c, if the leaflet 600 is in an invalid clamping state, that is, the leaflet 600 does not completely cover the probe opening 1321 on the clamping surface of the proximal clamp 1320, the distal end of the probe 1610 can be extended out from the probe opening 1321 and enter into the probe receiving cavity 1312 of the distal clamp 1310. The operator needs to re-clamp the leaflet 600. Therefore, the probe 1610 can effectively detect the clamping effect of the leaflet 600 by its mechanical structure, and the device has a simple structure and is convenient for operating.

As shown in FIG. 15, the probe 1610 can include a probe body 1661 having a certain length and a probe end 1662 disposed at a distal end of the probe body 1661. The probe body 1661 and the probe end 1662 are made of same materials or fixedly coupled therebetween. The probe body 1661 can be a solid or a hollow structure. The cross section of the probe body 1661 may be a regular circular or elliptical shape, a crescent shape, a semicircular shape, a polygonal shape, or the like, and is preferably a circular shape. The probe end 1662 is a solid structure or a hollow structure having a smooth outer surface. For convenience of pushing, the shape of the probe end 1662 is selected from at least one of a cone shape, a table shape, a column shape, a sphere shape, or a hemisphere shape. Both the probe body 1661 and the probe end 1662 may be made of metal materials, polymer materials, or metal-polymer composite materials. For example, the probe body 1661 may be a solid rod-shaped or hollow tubular structure of a single-layer or multiple layer composite structure, and may also be coiled from a single wire or a plurality of wires.

The hardness of the distal end of the probe body 1661 is less than or equal to the hardness of the proximal end of the probe body 1661. That is, the distal end of the probe body 1661 preferably has flexibility or resilience to avoid leaflet being stabbed or damaged, and the proximal end of the probe body 1661 is preferably a structure having a certain stiffness or stiffness to provide support and pushability.

In at least one embodiment, the detecting assembly 1600 can include only one probe 1610, or can include multiple probes 1610. The multiple probes 1610 can be drilled through one lumen of the pushing shaft 1210 together, ie, the pushing shaft 1210 has only one probe channel 1270, or can also be drilled through separately in different lumens of the pushing shaft 1210, ie, the pushing shaft 1210 has multiple probe channels 1270.

Figure 19A:
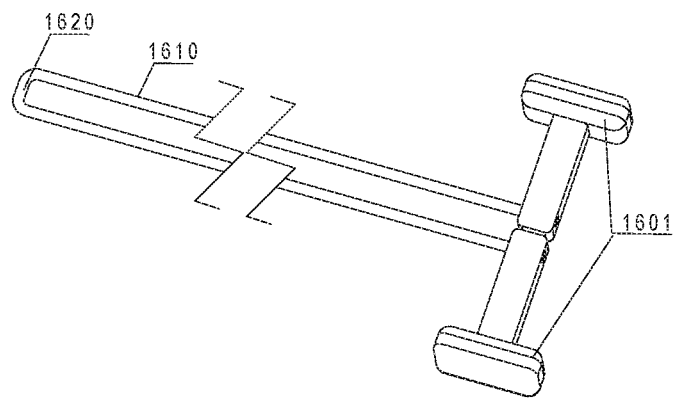
FIGS. 19a to 19c are structural schematic diagrams of the detecting assembly in another embodiment.
Figure 19B:
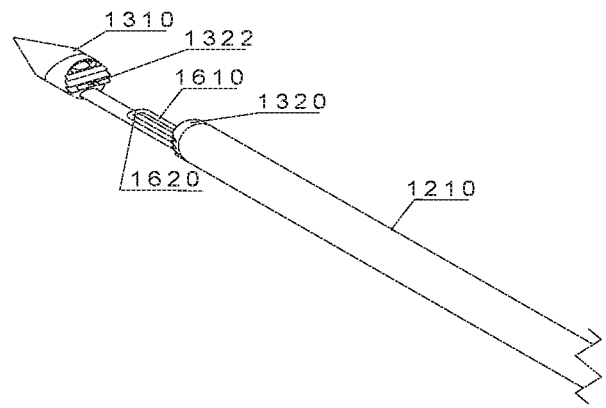
Figure 19C:
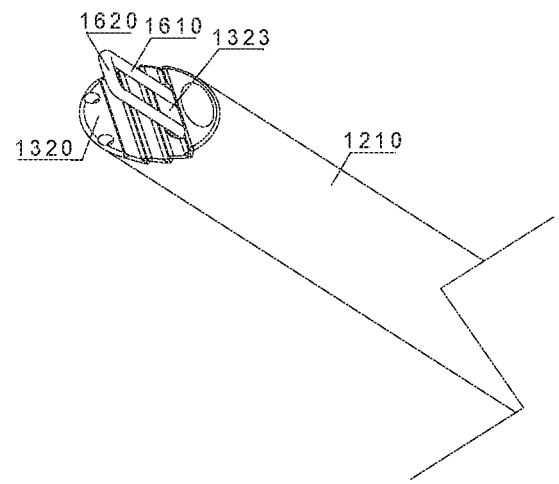

In at least one embodiment, the distal ends of two probes 1610 can be coupled to each other. As shown in FIG. 19a, the distal ends of the two probes 1610 can have certain elasticity/toughness, and are coupled together by a connecting rod 1620. When the fifth handle 1601 is withdrawn, the connecting rod 1620 is located on the clamping surface of the proximal clamp 1320. As shown in FIGS. 19b and 19c, the clamping surface of the proximal clamp 1320 preferably defines a probe groove 1323 for receiving the connecting rod 1620. The probe groove 1323 should be interconnected with the two probe channels 1270. Correspondingly, the clamping surface of the distal clamp 1310 defines a connecting rod receiving groove 1322 for receiving the connecting rod 1620. The connecting rod receiving groove 1322 is respectively interconnected with the two probe receiving cavities 1312. When the fifth handle 1601 of the detecting assembly 1600 is pushed to the distal end, the distal ends of the two probes 1610 and the connecting rod 1620 extend out of the proximal clamp 1320, and enter the two probe receiving cavities 1312 and the connecting rod receiving groove 1322 of the distal clamp 1310. When the fifth handle 1601 is withdrawn to the proximal end, the distal ends of the two probes 1610 and the connecting rod 1620 are withdrawn from the distal clamp 1310, the distal ends of the two probes 1610 each is received into the probe channel 1270 of the pushing shaft 1210, and the connecting rod 1620 is received on the clamping surface or the probe groove 1323 on the clamping surface of the proximal clamp 1320.

Figure 20:
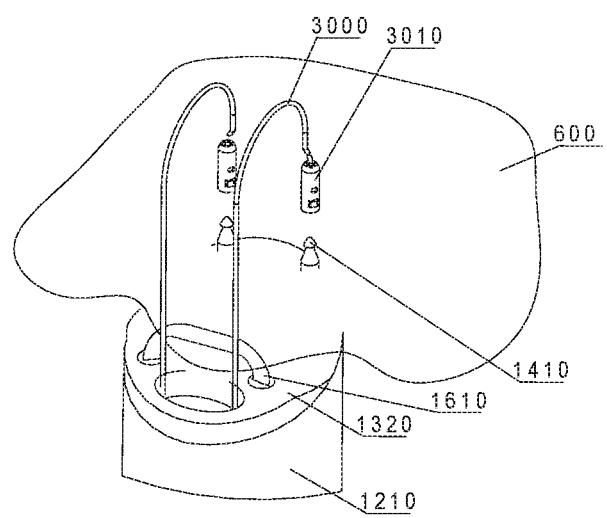

In this embodiment of the detecting assembly 1600, the contact area of the distal end of the detecting assembly 1600 and the leaflet is increased, and is particularly suitable for detecting irregular leaflet shapes. For example, as shown in FIG. 20, since the edge shape of the leaflet 600 is irregular, even if the leaflet 600 has been effectively clamped by the capturing assembly 1300, the leaflet 600 may not cover the probe outlet 1321 of the proximal clamp 1320, and the distal ends of the two probes 1610 of the present embodiment are coupled together by the connecting rod 1620, which increases the contact area between the distal end of the detecting assembly 1600 and the leaflet. It can detect that the leaflet has been clamped, which instructs the operator to perform the leaflet puncture and implant the suture 3000.

After the suture 3000 was implanted into the leaflet using the above suture implanting apparatus 1000, the suture 3000 was fixed by the suture locking apparatus 2000.

Figure 21:
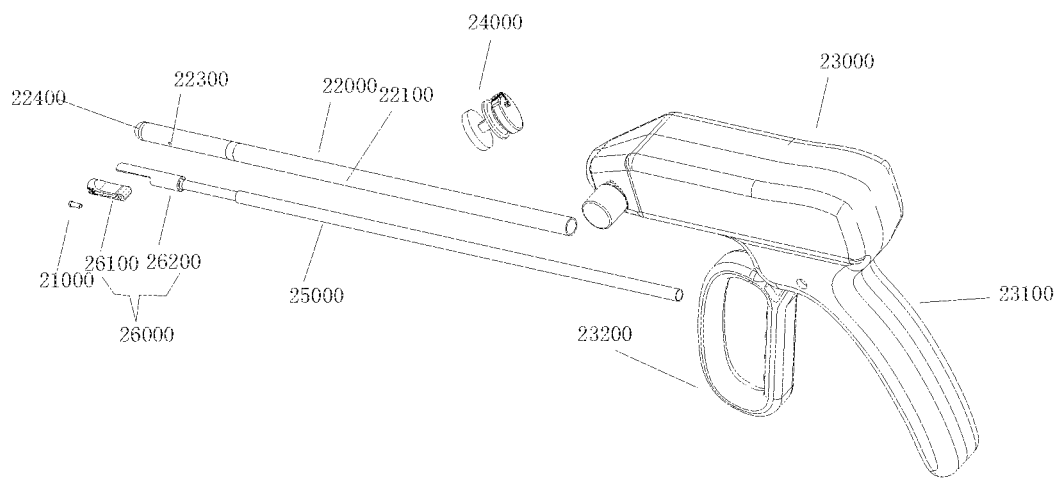
FIG. 21 is a structural schematic diagram of a suture locking apparatus of FIG. 3.
Figure 22:
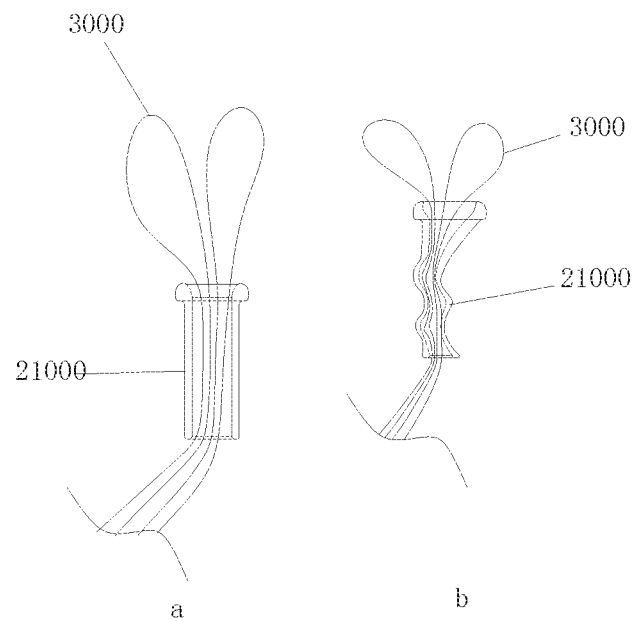
FIG. 22 is a schematic diagram of a lock pin of FIG. 21 before and after fixing the suture.
Figure 23:
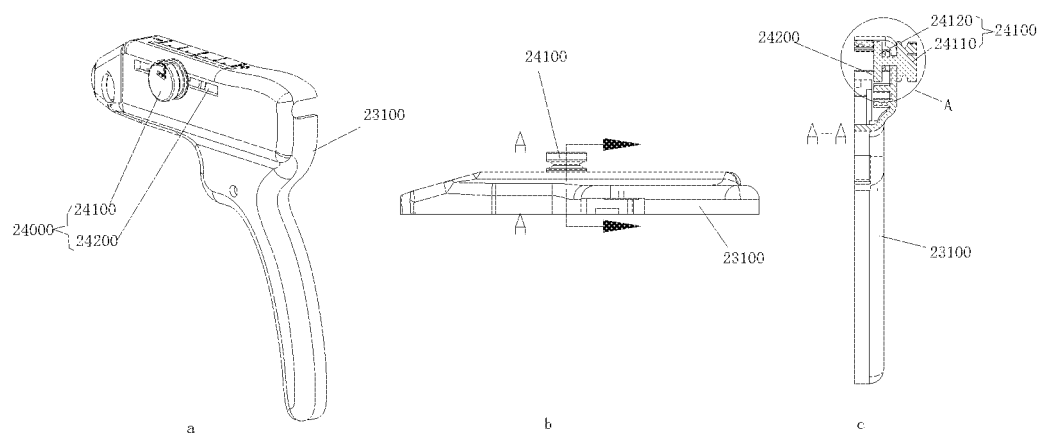
FIG. 23 is a structural schematic diagram showing a handle portion of the suture locking apparatus of FIG. 21.
Figure 35:
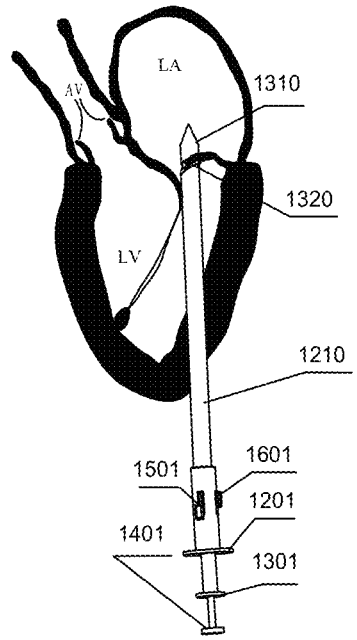

As shown in FIG. 21, the suture locking apparatus 2000 can include a lock pin 21000, an outer tube 22000, a handle 23000, and an adjusting mechanism 24000. The lock pin 21000 is used to accommodate or fix the suture 3000 (refer to the figure a or b in FIG. 22, where the figure a shows that before the fixing, the figure b shows the fixing). The outer tube 22000 defines a cavity 22100, and the lock pin 21000 is located at the distal end of the cavity 22100 (as shown in FIG. 35). The handle 23000 can include a fixing portion 23100 that is coupled to a proximal end of the outer tube 22000. The adjusting mechanism 24000 is located on the fixing portion 23100 (as shown in FIG. 23). The adjusting mechanism 24000 is coupled to the proximal end of the suture 3000, and is used for adjusting the tightening or loosening of the suture 3000. It can be understood that the adjusting mechanism 24000 can be any device capable of tightening or loosening the suture 3000. For example, a cable tie or a buckle. It can be understood that the number of the adjusting mechanism 24000 can be set according to need. Preferably, two adjusting mechanisms 24000 are disposed on two opposite sides of the fixing portion 23100 for adjusting two sets of sutures 3000 respectively.

In this embodiment, in the minimally invasive surgery or the interventional therapy, the suture locking apparatus 2000 can adjust the length of the sutures 3000 according to the efficacy in the process of fixing the sutures, thereby enhancing a surgical effect and improving a success rate of the surgery.

As shown in FIG. 23, in the further embodiment, the adjusting mechanism 24000 can include a cable tie 24100. The cable tie 24100 is movably coupled to the fixing portion 23100. The cable tie 24100 is coupled to the proximal end of the sutures 3000 to adjust the tightening or loosening of the sutures 3000. By adjusting the tightening or loosening of the sutures 3000 through the cable tie 24100, the length of the sutures 3000 can be effectively controlled, and the effect of adjusting the relatively small length can be achieved. For example, one cable tie 24100 is that the sutures 3000 are winded on the cable tie 24100, and the sutures 3000 are tightened or loosened by changing a winding direction or a winding way.

In the further embodiment, the adjusting mechanism 24000 can further include an adjustment guideway 24200 disposed on the fixing portion 23100. The cable tie 24100 is coupled to the fixing portion 23100 by the adjustment guideway 24200. The cable tie 24100 can slide in the adjustment guideway 24200 along an axial direction of the adjustment guideway 24200, thereby adjusting the tightening or loosening of the sutures 3000. It will be appreciated that the cable tie 24100 adjusts the tightening or loosening of the sutures 3000 by rolling in the adjustment guideway 24200. It can be understood that the axial direction of the adjustment guideway 24200 coincides with the overall axial direction of the suture locking apparatus 2100 or has a preset angle to allow the cable tie 24100 to roll in the adjustment guideway 24200 to adjust the tightening or loosening of the sutures 3000. The overall axial direction of the suture locking apparatus 2000 refers to the direction from the proximal end to the distal end.

Figure 24:
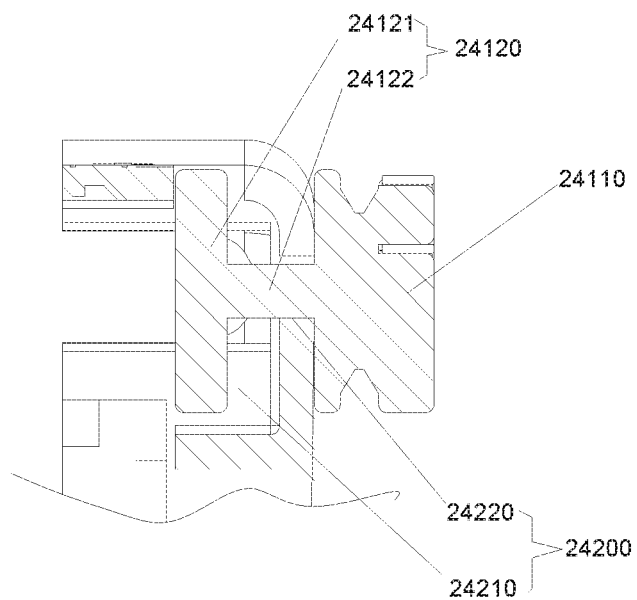
FIG. 24 is a partial enlarged view of a portion A in a c figure in FIG. 23.

As shown in FIGS. 23 and 24, in the further embodiment, the cable tie 24100 can include a suture fixing portion 24110 and a handle connecting portion 24120. The suture fixing portion 24110 is detachably coupled to the sutures 3000. Therein, the sutures 3000 can be fixed to the suture fixing portion 24110 by winding, pressing, crimping, or the like. The handle connecting portion 24120 is located in the adjustment guideway 24200. The cable tie 24100 can slide in the adjustment guideway 24200 in the axial direction of the adjustment guideway 24200 through the handle connection portion 24120. The handle connecting portion 24120 is located in the adjustment guideway 24200 by a snapping or the like to ensure that the cable tie 24100 does not fall off the handle 3000. The handle connecting portion 24120 can include an embedding end 24121 and a connecting shaft 24122. The embedding end 24121 is located in the guideway cavity 24210 and can slide in the axial direction. The connecting shaft 24122 is located on a guideway outer wall 24220 and can slide in the axial direction. The embedding end 24121 is coupled with the suture fixing portion 24110 through the connecting shaft 24122.

Figure 25:
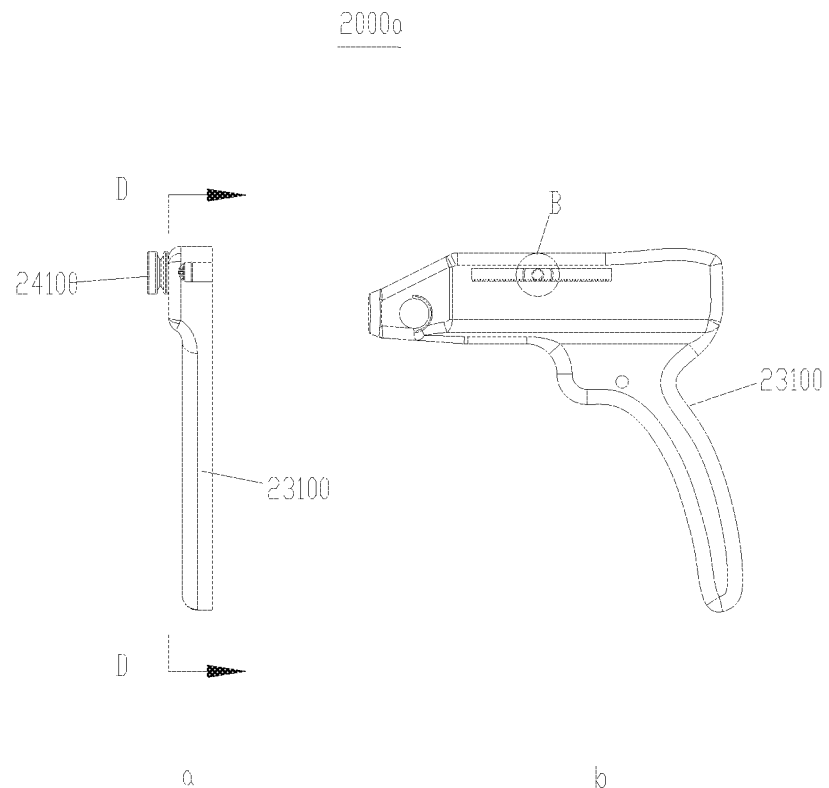
FIG. 25 is a structural schematic diagram of a handle portion in another embodiment of the suture locking apparatus, wherein b figure is a D-D cross-sectional view of a figure.
Figure 26:
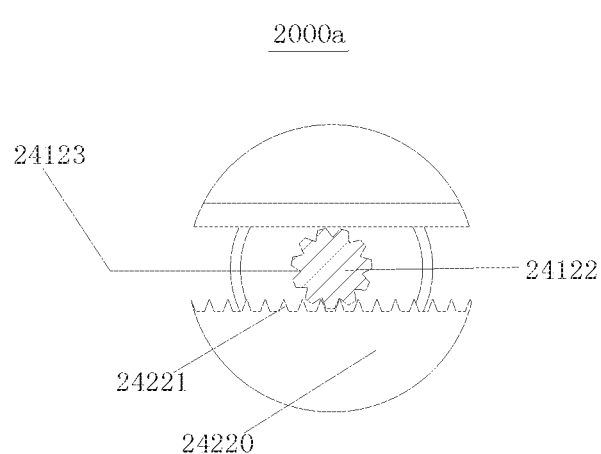
FIG. 26 is a partial enlarged view of a portion B in the diagram of b in FIG. 25.

As shown in FIGS. 25 and 26, another embodiment of the suture locking apparatus 2000a is shown. The figure a in FIG. 25 is a right view from the direction of the handle of the suture locking apparatus 2000a. The figure b in FIG. 25 is a D-D cross-sectional view of the FIG. 25. FIG. 26 is a partial enlarged view of the figure b of FIG. 25 at B. The suture locking apparatus 2000a differs from the first suture locking apparatus 2000 in that the adjustment guideway 24200 can include a guideway cavity 24210 and a guideway outer wall 24220. The guideway outer wall 24220 can include first teeth 24221. The connecting shaft 24122 can include second teeth 24123. The first teeth 24221 engage with the second teeth 24123 to roll the connecting shaft 24122 on the guideway outer wall 24220. Further, the cable tie 24100 can slide in the adjustment guideway 24200 to advance or retract along the axial direction thereof. When the operator rotates the cable tie 24100, the cable tie 24100 moves axially along the adjustment guideway 24200, and a rotational motion of the cable tie 24100 can be converted into a linear motion of the suture 3000, thereby accurately achieving the tightening and loosening of the suture 3000.

Figure 27:
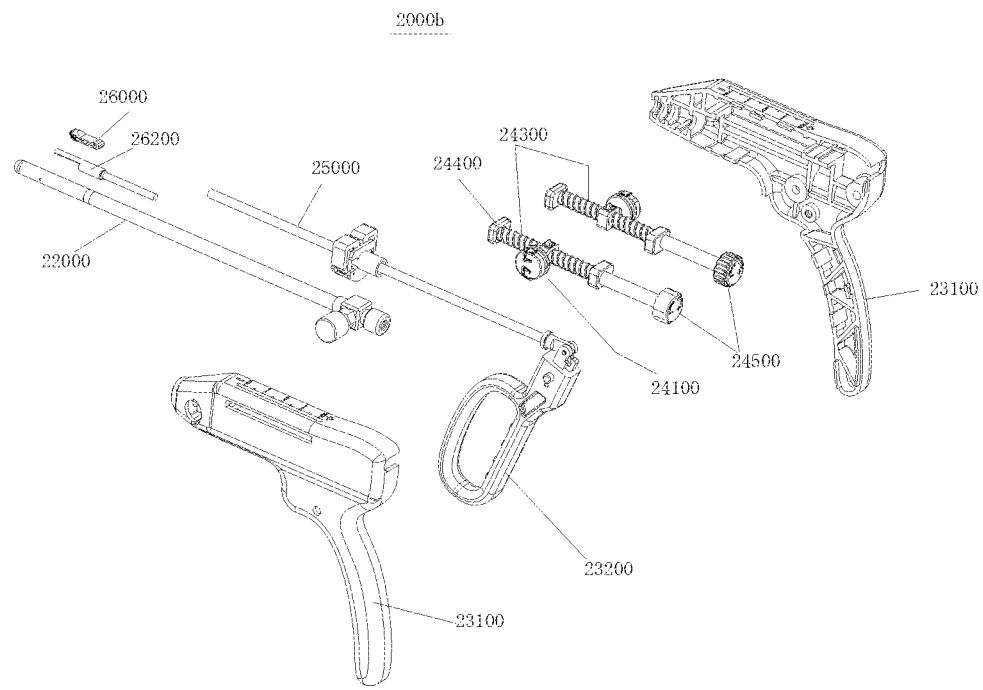
FIG. 27 is an exploded structural schematic diagram showing the handle portion in another embodiment of the suture locking apparatus.
Figure 28:
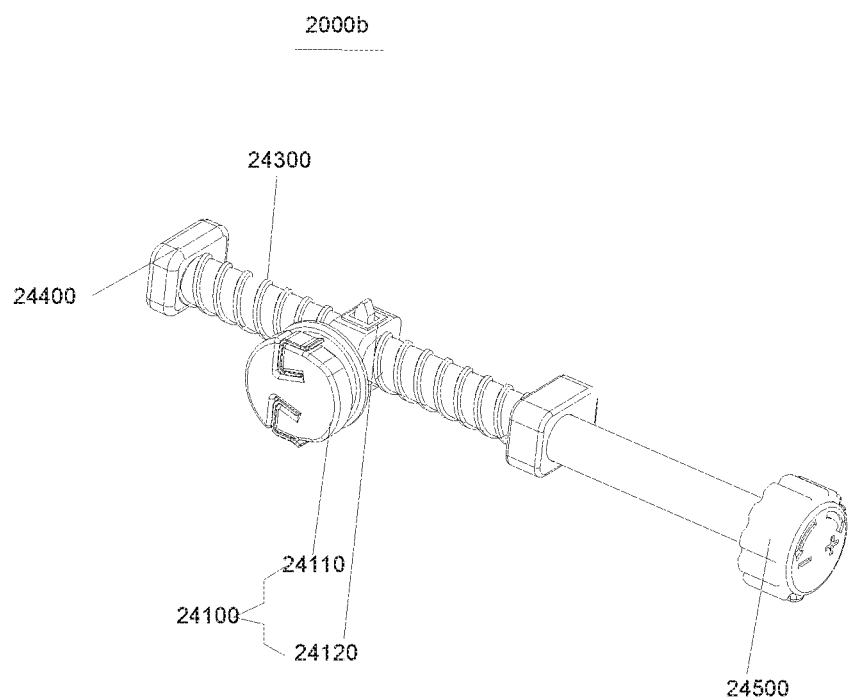
FIG. 28 is a structural schematic diagram of an adjusting mechanism in the suture locking apparatus of FIG. 27.

As shown in FIGS. 27 and 28, another embodiment of the suture locking apparatus 2000b is shown. The suture locking apparatus 2000b differs from the suture locking apparatus 2000 in that the adjusting mechanism 24000 can further include a lead screw 24300, a bolt 24400, and an adjustment knob 24500. The lead screw 24300 is fixed in the fixing portion 23100 along the axial direction of the adjustment guideway 24200. The bolt 24400 is fixed in the fixing portion 23100, and the lead screw 24300 passes through the bolt 24400 and is fitted with the bolt 24400. The proximal end of the lead screw 24300 passes through the proximal end of the fixing portion 23100 and is coupled to the adjustment knob 24500. The handle connecting portion 24120 is fixed to the lead screw 24300. The adjustment knob 24500 adjusts the lead screw 24300 to advance or retreat in the axial direction of the adjustment guideway 24200. When the operator rotates the adjustment knob 24500, the adjustment knob 24500 drives the lead screw 24300 to rotate in the fixing portion 23100, thereby driving the cable tie 24100 coupled to the lead screw 24300 to advance or retreat in the axial direction of the adjustment guideway 24200.

Figure 29:
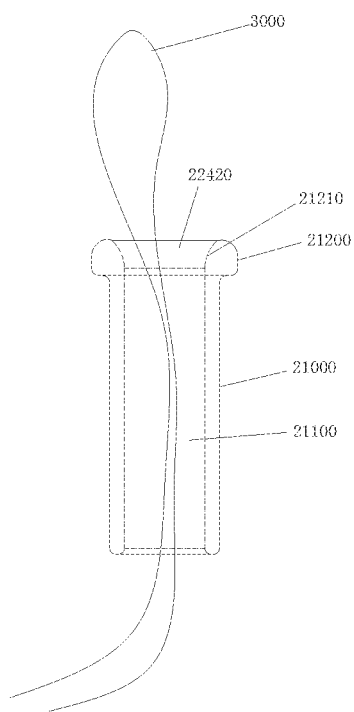
FIG. 29 is a cross-sectional view showing the lock pin in the suture locking apparatus of FIG. 21.

As shown in FIG. 21 again, in further embodiment, the handle 23000 can further include a movable portion 23200. The movable portion 23200 and the fixing portion 23100 are relatively movable. The lock pin 21000 can define a hollow inner cavity 21100 (as shown in FIG. 29) in the axial direction thereof. The hollow inner cavity 21100 is used to receive and pass through the suture 3000. The suture locking apparatus 2000 can also include a crimping assembly 26000 and a mandrel 25000. The crimping assembly 26000 is for holding the lock pin 21000 and deforming the lock pin 21000 (refer to FIG. 22, wherein figure a in FIG. 22 indicates before deformation, and figure b in FIG. 22 indicates deformation). When the lock pin 21000 is subjected to a mechanical external force, it can be compressed to fix the sutures 3000 in the lock pin 21000. It will not move relative to the lock pin 21000, thus locking and fixing the sutures 3000. The lock pin 21000 may be of various shapes, for example, a cylindrical shape, a prism shape, or the like, as long as it has a hollow inner cavity 21100 for accommodating any shape of the suture 3000. A cylindrical shape is employed in this embodiment to reduce the crimp resistance.

The distal end of the mandrel 25000 is coupled to the proximal end of the crimping assembly 26000, and the proximal end of the mandrel 25000 is movably coupled to the movable portion 23200. The crimping assembly 26000 and the mandrel 25000 are located in the cavity 22100, and the movable portion 23200 moves relative to the fixing portion 23100 to drive the mandrel 25000 to move, causing the crimping assembly 26000 to press the lock pin 21000. It can be understood that the mandrel 25000 applies a force to the crimping assembly 26000 during the movement, so that the crimping assembly 26000 has a mechanical external force of crimping the lock pin 21000, so as to press the lock pin 21000. Where the mandrel 25000 can be extended into the fixing portion 23100, a movable connection portion 23210 between the movable portion 23200 and the mandrel 25000 is located in the fixing portion 23100 (refer to FIG. 31*a* and FIG. 31*b*).

Figure 30:
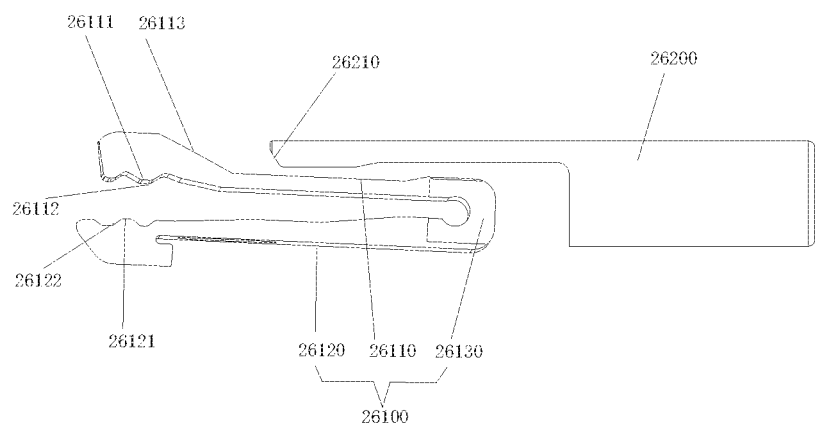
FIG. 30 is a structural schematic diagram showing a crimping assembly in the suture locking apparatus of FIG. 21.
Figure 32:
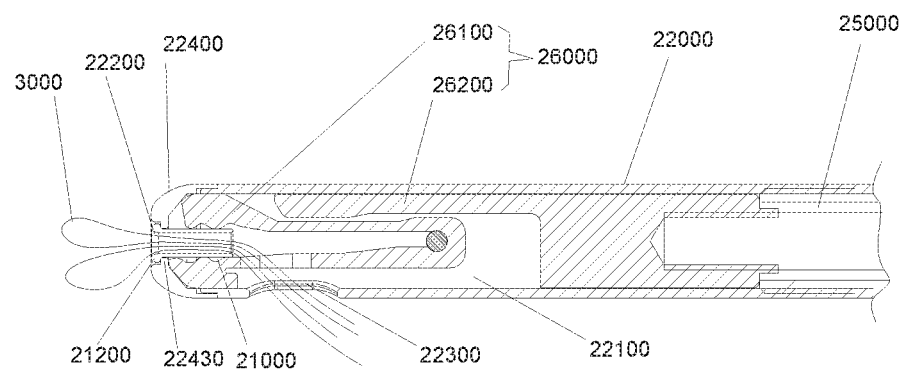
Figure 32:
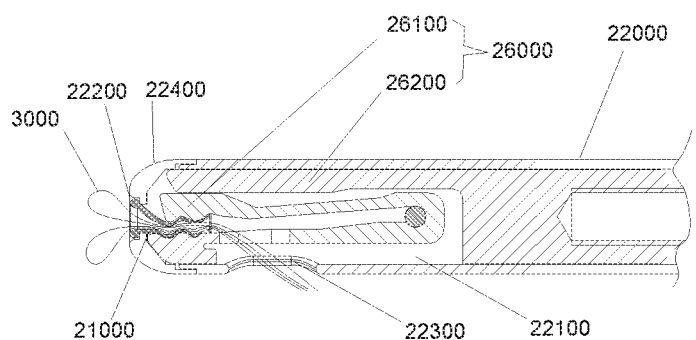

As shown in FIGS. 30 and 32, in the further embodiment, the crimping assembly 26000 can include a crimping clamp 26100 and a crimping rod 26200. The crimping clamp 26100 can include an upper clamping piece 26110, a bottom clamping piece 26120, and a clip connecting portion 26130 coupling the upper clamping piece 26110 and the bottom clamping piece 26120. The lock pin 21000 is received between the upper clamping piece 26110 and the bottom clamping piece 26120. The proximal end of the crimping rod 26200 is coupled to the distal end of the mandrel 25000. The distal end of the crimping rod 26200 is located close to the upper clamping piece 26110. The mandrel 25000 drives the crimping rod 26200 to move towards the upper clamping piece 26110, which cause the upper clamping piece 26110 to move towards the bottom clamping piece 26120 to make the upper clamping piece 26110 and the bottom clamping piece 26120 cooperatively crimp the lock pin 21000. The crimping rod 26200 is made of stainless steel, nickel titanium alloy or cobalt chromium alloy, preferably made of stainless steel.

In at least one embodiment, the upper clamping piece 26110 and/or the bottom clamping piece 26120 are at least partially made of deformable materials with certain elasticity. Therefore, the upper clamping piece 26110 and/or the bottom clamping piece 26120 are deformable when subjected to an external force. The upper clamping piece 26110 and/or the bottom clamping piece 26120 may be brought closer together, and the lock pin 21000 placed between the upper clamping piece 26110 and the bottom clamping piece 26120 is crimped into a shape having a certain curvature. It can be understood that the upper clamping piece 26110 and the bottom clamping piece 26120 are preferably made of stainless steel, nickel titanium alloy, cobalt chromium alloy or the like, and the clip connecting portion 26130 is made of stainless steel, nickel titanium alloy or the like. In this embodiment, the whole crimping clamps 26100 are made of nickel-titanium alloy.

As shown in FIG. 30, in the further embodiment, the upper clamping piece 26110 can include a first surface 26111 that faces the lock pin 21000, and the bottom clamping piece 26120 can include a second surface 26121 that faces the lock pin 21000. The first surface 26111 can include a first engaging portion 26112. The second surface 26121 can include a second engaging portion 26122. The first engaging portion 26112 is engaged with the second engaging portion 26122 such that the upper clamping piece 26110 and the bottom clamping piece 26120 can be in the close state. It can be understood that the first engaging portion 26112 and the second engaging portion 26122 may have a curvature shape or a sawtooth shape that cooperate with each other.

Figure 31:
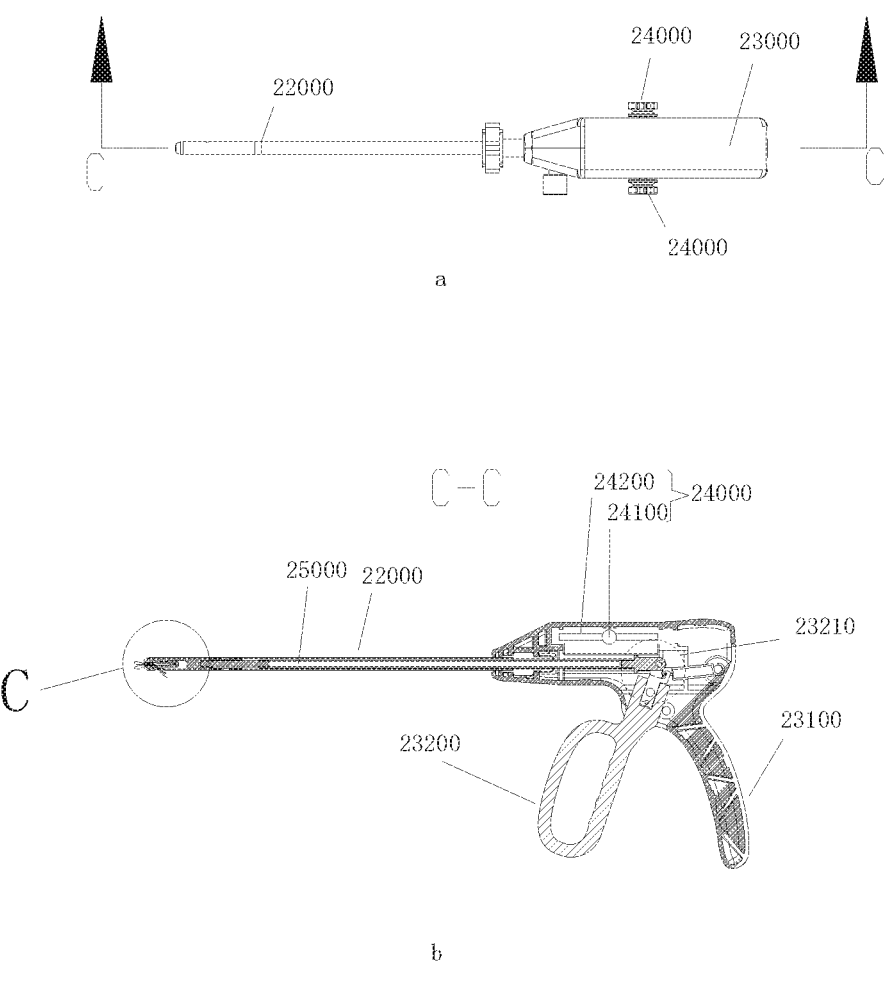
FIG. 31a and FIG. 31b are schematic diagrams showing a process of the suture locking apparatus of FIG. 21 for holding the lock pin.

As shown in FIG. 31*a*, FIG. 31*b*, FIG. 32*a* and FIG. 32*b*, FIG. 32*a* and FIG. 32*b* are partial enlarged views of b figure in FIG. 31*a* and FIG. 31*b*. In a further embodiment, the distal end of the outer tube 22000 defines a suture inlet 22200 radially. A diameter of the suture inlet 22200 is at least equal to the diameter of the largest outer diameter of the lock pin 21000, so that the lock pin 21000 after the crimping can be detached from the distal end of the outer tube 22000. The outer tube 22000 further defines a suture outlet 22300. The suture inlet 22200 and the suture outlet 22300 are both interconnected with the hollow inner cavity 21100 of the lock pin 21000, so that the proximal ends of the sutures 3000 can sequentially pass through the suture inlet 22200, the distal end of the lock pin 21000, and the suture outlet 22300. It can be understood that, in other embodiments, the suture outlet 22300 can be disposed at any position of the outer tube 22000, or disposed on the handle 23000, as long as the suture outlet 22300 is coupled to the hollow inner cavity 21100 of the lock pin 21000, the suture 3000 can be passed through the proximal end of the suture outlet 22300.

When using the suture locking apparatus 2000, the operator drives the proximal ends of the sutures 3000 to pass through the suture inlet 22200 of distal end of the outer tube 22000, the opening of the distal end of the lock pin 21000, and the suture outlet 22300 of the distal end of the outer tube 22000, and then fixes the sutures 3000 to the suture fixing portion 24110 of the cable tie 24100. The length of the suture 3000 is adjusted by the adjusting mechanism 24000 according to need. When the adjustment is completed, the movable portion 23200 of the handle 23000 is driven to move towards the fixing portion 23100, thereby driving the mandrel 25000 to move toward the distal end of the outer tube 22000, thereby causing the crimping rod 26200 to press the crimping clamp 26100, the upper clamping piece 26110 and the bottom clamping piece 26120 of the crimping clamp 26100 to press the lock pin 21000, so that the lock pin 21000 is deformed (refer to FIG. 32*a* and FIG. 32*b*, the figure a in FIG. 32*a* and FIG. 32*b* is before the pressure is held, and the figure b in FIG. 32a and FIG. 32b is after the pressure grip), the sutures 3000 received in lock pin 21000 is fixed with lock pin 21000.

As shown in FIG. 46, the following is a schematic flow chart of a heart valve repair method provided in this embodiment for repairing a mitral valve. The heart valve repair method is applied to the heart valve repair system 100.

Step S1: the distal end of the suture implanting apparatus 1000 is advanced from an outside of a body through a transapical approach into a left ventricle of a heart.

Figures 33, 34:
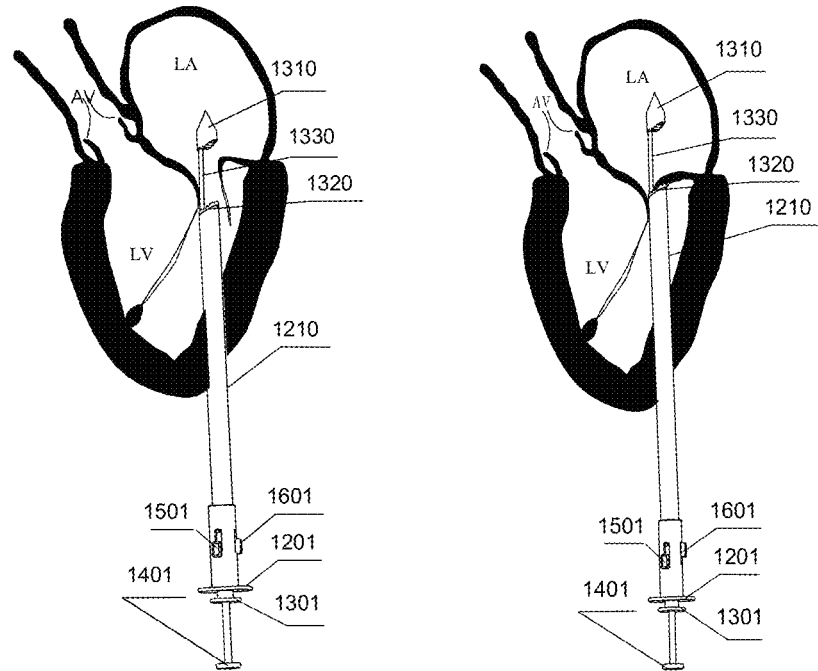

In detail, referring to FIG. 33, after a transapical puncture, the distal end of the suture implanting apparatus 1000 is advanced through the apex into the left ventricle until the distal clamp 1310 and the proximal clamp 1320 are both located in a left atrium.

Step S2: each leaflet of a heart valve is held with the distal end of the suture implanting apparatus 1000.

In detail, the capturing rod 1330 is pushed to separate the distal clamp 1310 from the proximal clamp 1320 and clamp each leaflet of the mitral valve. During the pushing of the capturing rod 1330 to separate the distal clamp 1310 from the proximal clamp 1320 and clamping the leaflet, the gripping auxiliary assembly 1500 is pushed to support the leaflet for assistance.

In detail, referring to FIG. 34, the pushing shaft 1210 is withdrawn to the proximal end or the capturing rod 1330 is pushed to the distal end, so that the proximal clamp 1320 is separated from the distal clamp 1310, and the fourth handle 1501 is pushed to the distal end, the fourth handle 1501 drives the gripping arm 1520 to push the gripping member 1510 out from the opening 1260. At this time, the gripping member 1510 is supported on the lower surface of the leaflet to stable the beating leaflet (as shown in FIG. 13b), the relative position between the first handle 1201, the second handle 1301 and the fourth handle 1501 is kept unchanged, and the entire suture implanting apparatus 1000 is slowly moved to the proximal end until the leaflet enters the space formed between the proximal clamp 1320 and the distal clamp 1310, and the gripping member 1510 can provide some support to the leaflet. Referring to FIG. 35, the distal end of the suture implanting apparatus 1000 is slightly moved until the edge of the leaflet contacts the capturing rod 1330. At this time, the second handle 1301 is withdrawn toward the proximal end, and the distal clamp 1310 is driven to the proximal clamp 1320 until the two are closed, and the leaflet is clamped.

Alternatively, the position of the leaflet is positioned by X-rays prior to clamping the leaflet, and then the leaflet is held using the proximal clamp 1320 and the distal clamp 1310.

Step S3 (optionally): the current clamping state of the leaflet is detected. When it is detected that the current clamping state of the leaflet is an effective clamping state, the process proceeds to step S5, otherwise, the process proceeds to step S4.

In detail, the probe 1610 is used to detect the current clamping state of the leaflet. When the probe 1610 detects that the current clamping state of the leaflet is the effective clamping state, the process proceeds to step S5, otherwise, the process proceeds to step S4.

Furthermore, the position of the first handle 1201 is kept unchanged, the fifth handle 1601 is pushed toward the distal end, and the probe 1610 is moved along the axial direction of the pushing shaft 1210 toward the distal end to detect the current clamping state of the leaflet.

Step S4 (optionally): the clamping position that the leaflet held by the suture implanting apparatus 1000 is re-adjusted, and the current clamping state of the leaflet is detected again to determine whether the current clamping state of the leaflet is an effective clamping state, if yes, the process proceeds to step S5, otherwise, the process continues to step S4.

In detail, when the current clamping state of the leaflet is detected as the ineffective clamping state, that is, the leaflet does not completely cover the probe outlet 1321 on the clamping surface of the proximal clamp 1320, the distal end of the probe 1610 may protrude from the probe outlet 1321 and enter the probe receiving cavity 1312 of the distal clamp 1310. The position between the distal clamp 1310 and the proximal clamp 1320 is adjusted such that there is a certain distance therebetween, and the relative position between the capturing rod 1330 and the leaflet is adjusted, and the leaflet is clamped by the distal clamp 1310 and the proximal clamp 1320 again. The probe 1610 is used to detect the current clamping state of the leaflet until the probe 1610 detects that the current clamping state of the leaflet is the effective clamping state, that is, the leaflet completely covers the probe outlet 1321 on the clamping surface of the proximal clamp 1320, the distal end of the probe 1610 cannot protrude from the probe outlet 1321 and enter the probe receiving cavity 1312 of the distal clamp 1310, and proceeds to step S5, otherwise, the step continues to step S4.

During the adjustment process, since the gripping auxiliary assembly 1500 under the leaflet has a certain supporting effect on the leaflet, the leaflet can be prevented from slipping out of the capturing assembly 1300, that is, slipping out between the distal clamp 1310 and the proximal clamp 1320.

Step S5: the suture 3000 is implanted into the leaflet.

In detail, the puncturing rod 1420 is driven to drive the puncturing needle 1410 to puncture the leaflet, and is then coupled with the fixing member 3010 of the suture 3000, and the puncturing rod 1420 is withdrawn to drive the fixing member 3010 and the sutures 3000 to pass through the leaflet, so as to implant the sutures 3000 into the leaflet.

Optionally, the heart valve repair method further includes:

When the puncturing rod 1420 is withdrawn to drive the fixing member 3010 and the sutures 3000 through the leaflet, the anti-slip member 3020 does not pass through the leaflet and the contact surface 3021 of the anti-slip member 3020 fits the upper surface of the leaflet.

Figures 36, 37:
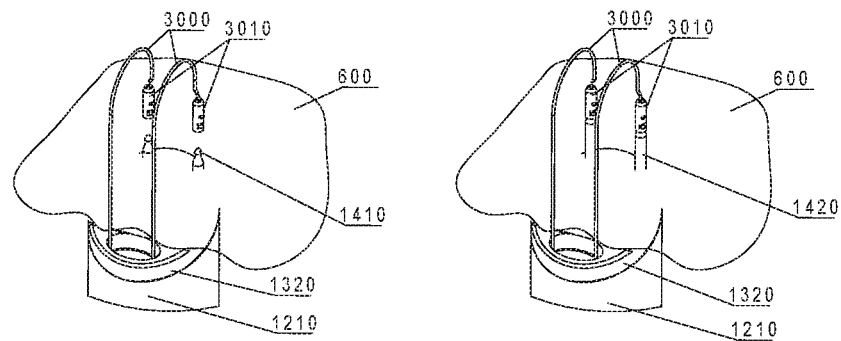
Figure 38:
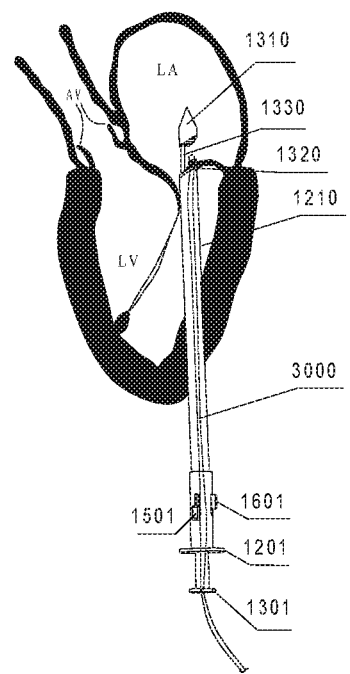
Figure 39:
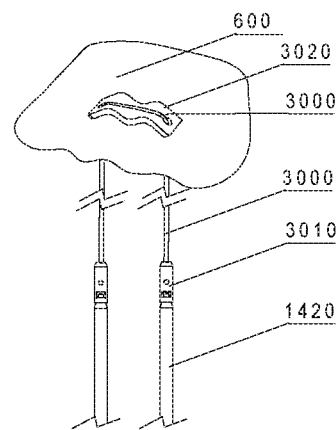

In detail, as shown in FIGS. 36 and 37, the third handle 1401 is pushed toward the distal end, and the puncturing needle 1410 is driven to move toward the distal end until the puncturing needle 1410 passes through the leaflet and forms a fixed connection with the fixing member 3010 of the suture 3000. Referring to FIG. 38 and FIG. 39, the third handle 1401 is withdrawn, so that the puncturing needle 1410 drives the fixing member 3010 of the suture 3000 and the suture 3000 coupled with the fixing member 3010 through the leaflet in turn, and the anti-slip member 1130 is also pulled out from the clamping surface of the distal clamp 1310, the contact surface of the anti-slip member 1130 is in contact with the upper surface of the leaflet, and a part of the suture 3000 presses against the upper surface of the anti-slip member 1130 to fit the leaflet. At this time, the point contact between the suture 3000 and the leaflet is changed to the surface contact between the anti-slip member 1130 and the leaflet, which can effectively reduce the risk of leaflet tearing.

Step S6: the distal end of the suture implanting apparatus 1000 is withdrawn from the body.

In detail, the third handle 1401 is continuously withdrawn until the fixing member 3010 is withdrawn from the proximal end of the pushing shaft 1210, and then the fourth handle 1501 is withdrawn, the gripping member 1510 is withdrawn to the gripping arm receiving space 1250, and the entire suture implanting apparatus 1000 is withdrawn, so as to complete to implant the suture 3000 on one leaflet of the mitral valve.

Optionally, when performing the chordae repair, the method further comprises the steps of: adjusting the length of the sutures 3000 remaining in the heart, and fixing the proximal end of the sutures 3000 to the ventricular wall or the papillary muscle.

Step S7: the operations of steps S1 to S6 are repeated, the other side leaflet of the heart valve is held with the distal end of the suture implanting apparatus 1000, and at least the other suture 3000 is implanted into the other side leaflet.

Step S8: the distal end of the suture locking apparatus 2000 is advanced from the outside of the body through the transapical approach into the left ventricle.

Figure 40:
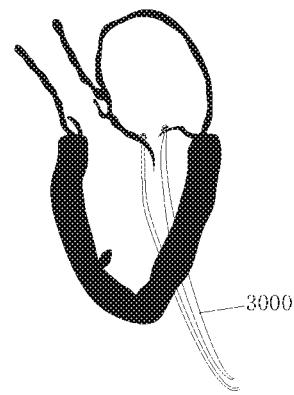
Figure 41:
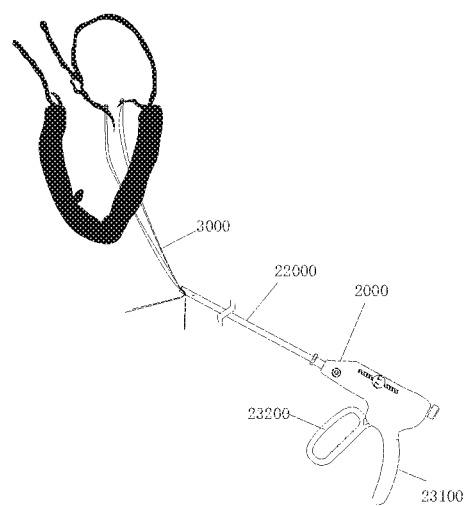

In detail, referring to FIG. 40, a plurality of sutures 3000 on both leaflets are inserted into the lock pin 21000 of the suture locking apparatus 2000b in vitro, and the proximal ends of the sutures 3000 are passed through the suture outlet 22300 on the distal end of the outer tube 22000 (as shown in FIG. 41), the sutures 3000 on the anterior leaflet and posterior leaflet are distinguished, the proximal ends of the two sets of sutures 3000 are wrapped on a cable tie 24100 for several turns, and then the proximal end of the sutures 3000 are fixed on the cable tie 24100 to maintain the relative position between the sutures 3000 and the lock pin 21000.

Figure 42:
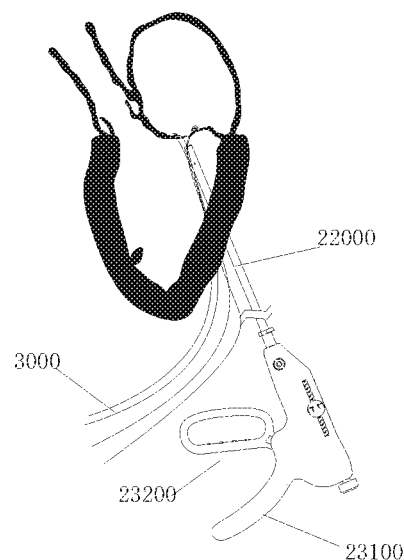
Figure 43:
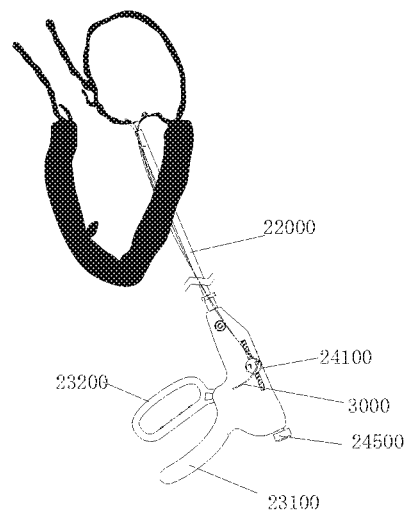

The distal end of the suture locking apparatus 2000b is advanced through the apex into the heart, is driven to move closer to the leaflet of the mitral valve, and the sutures 3000 are pulled until the distal end of the suture locking apparatus 2000b reaches a predetermined position under the mitral valve. It can be understood that after the sutures 3000 are passed through the suture outlet 22300, the distal end of the suture locking apparatus 2000b is first pushed into the heart through the apex, and moved toward the leaflet of the mitral valve (as shown in FIG. 42), and then the sutures 3000 are fixed on the cable tie 24100.

Step S9 (optionally): the relative position of the plurality of sutures 3000 is adjusted by the suture locking apparatus 2000b.

In detail, the plurality of sutures 3000 correspondingly implanted into different leaflets are inserted into the lock pin 21000 of the suture locking apparatus 2000b in vitro, and the relative position between the plurality of sutures 3000 and the lock pin 21000 is adjusted. And, when adjusting the relative position between the plurality of sutures 3000 and the lock pin 21000, the state of the valve regurgitation is determined to be a slightest state or complete elimination by a medical imaging device such as medical ultrasound equipment, and when the slightest state or complete elimination is reached, the relative position between the plurality of sutures 3000 and the lock pin 21000 are maintained.

In detail, the plurality of sutures 3000 correspondingly implanted on different leaflets are inserted into the lock pin 21000 in vitro and the adjusting mechanism 24000 adjusts the relative position between the plurality of sutures 3000 and the lock pin 21000. After the lock pin 21000 is crimped by the crimping assembly 26000 and the lock pin 21000 is deformed to lock the plurality of sutures 3000 in the corresponding left ventricle. And, when the relative position between the plurality of sutures 3000 and the lock pin 21000 is adjusted by the adjusting mechanism 24000, the state of the valve regurgitation is determined to be the slightest state or complete elimination by the medical imaging device such as medical ultrasound equipment, and when the slightest state or complete elimination is reached, the relative positions between the plurality of sutures 3000 and the lock pin 21000 are maintained, and the lock pin 21000 is pressed by the crimping assembly 26000 and the lock pin 21000 is deformed to lock the plurality of sutures 3000 in a corresponding place of the left ventricle.

More specifically, two adjustment knobs 24500 are respectively rotated to drive the two lead screws 24300 to rotate, thereby driving the cable tie 24100 coupled to the lead screw 24300 to move back and forth in the axial direction of the adjustment guideway 24200 to respectively adjust two sets of sutures 3000 coupled to the cable tie 24100 to determine the slightest state or complete elimination of the valve regurgitation by ultrasound. When the slightest state or complete elimination is reached, the rotation of the adjustment knob 24500 is stopped, and the tension of the two sets of sutures 3000 can be maintained, that is, the relative distance of the leaflets between the two sides of the mitral valve is maintained.

Step S10: the plurality of sutures 3000 are locked in the left ventricle with the distal end of the suture locking apparatus 2000b.

In detail, as shown in FIG. 31a, FIG. 31b, FIG. 32a, FIG. 32b and FIG. 43, the fixing portion 23100 of the handle 23000 is kept stationary, and the movable portion 23200 is moved to the fixing portion 23100 until the movable portion 23200 cannot continue to move. At this time, the mandrel 25000 and the crimping rod 26200 are opposed to the outer tube 22000 moving toward the distal end, the distal end of the crimping rod 26200 continues to squeeze the crimping clamp 26100 so that the upper clamping piece 26110 and the bottom clamping piece 26120 of the crimping clamp 26100 are close together, and the lock pin 21000 between the upper clamping piece 26110 and the bottom clamping piece 26120 is pressed until the lock pin 21000 is deformed, the sutures 3000 in the lock pin 21000 are fixed together, and the deformed lock pin 21000 is released from the suture inlet 22200 of the distal end of the outer tube 22000 of the suture locking apparatus 2000b.

Step S11: the distal end of the suture locking apparatus 2000b is withdrawn from the body.

Figure 44:
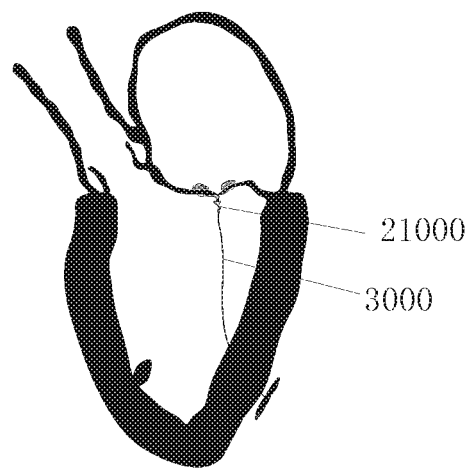

After the plurality of sutures 3000 are locked in the left ventricle through the lock pin 21000, the lock pin 21000 is left in the left ventricle, and the distal end of the suture locking apparatus 2000 is withdrawn from the body, and the proximal ends of the sutures 3000 locked by the lock pin 21000 are fixed on the ventricular wall or the papillary muscle (as shown in FIG. 44), and the anterior leaflet 1010 and the posterior leaflet 1020 of the mitral valve form a double orifice structure to complete the edge-to-edge mitral valve repair (also called Alfieri stitch).

Figure 45:
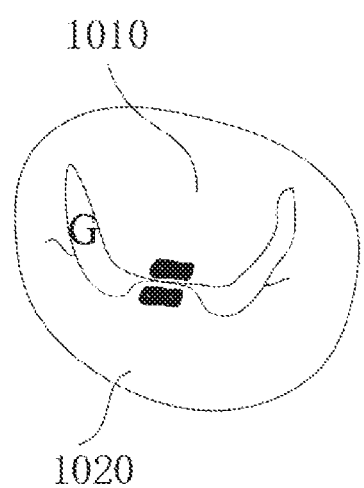

It can be understood that, in this step, after the plurality of sutures 3000 are locked in the left ventricle through the lock pin 21000, the lock pin 21000 may be left in the left ventricle. The distal end of the suture locking apparatus 2000b is withdrawn from the body, and the proximal ends of the sutures 3000 locked by the lock pin 21000 are cut off from the proximal end of the lock pin 21000 (as shown in FIG. 45).

It will be appreciated that the heart valve repair method of other embodiments of the present disclosure can also be used to reduce or treat the "tricuspid regurgitation" of the right ventricle, ie, the three leaflets of the tricuspid valve to the right ventricle by suture implanting apparatus, one or more sutures are implanted respectively, and the sutures on the three leaflets are fixed together by the suture locking apparatus, thereby reducing or avoiding "tricuspid regurgitation". The principle and structure of the heart valve repair method for solving the mitral regurgitation in the embodiment of the present disclosure are basically the same, and will not be described herein. It will be appreciated that the heart valve repair method of other embodiments of the present disclosure can be applied to other minimally invasive surgical procedures that require suture implantation into several sheet-like tissues and fixation of the suture, respectively.

In summary, the heart valve repair method of the present disclosure first implants multiple sutures on each leaflet of the mitral valve or tricuspid valve, and then fixes the multiple sutures together by the suture locking apparatus to reduce or eliminate the gap between the mitral/tricuspid valve for the treatment of mitral regurgitation or tricuspid regurgitation, simple surgical procedure, low surgical cost, low patient trauma, low risk of complications, and rapid recovery. In addition, the operator can adjust the tightening or loosening of the sutures before fixing the suture, thereby adjusting the gap between the leaflets of the mitral or tricuspid valve, and observing the regurgitation of the mitral or tricuspid valve through the medical imaging device. When the state of the regurgitation is reached to the slightest state or complete elimination, the lock pin fixes the sutures, thereby realizing the adjustable function of the mitral or tricuspid regurgitation.

The above is a preferred embodiment of the present disclosure, and it should be noted that those skilled in the art may make some improvements and modifications without departing from the principle of the present disclosure, and these improvements and modifications are also the protection scope of the present disclosure.

What is claimed is:

1. A heart valve repair method, applied to a heart valve repair system, the heart valve repair system comprising a plurality of sutures and a suture implanting apparatus, at least one end of the suture being provided with at least one fixing member respectively, the suture implanting apparatus comprising a capturing assembly, a puncturing assembly, and a pushing shaft, the pushing shaft axially defining a plurality of lumens, the puncturing assembly and the capturing assembly being movably received in different lumens of the pushing shaft, the capturing assembly comprising a capturing rod, a distal clamp and a proximal clamp, the plurality of sutures being received in the capturing rod and extending out from the distal clamp, the puncturing assembly comprising a puncturing needle and a puncturing rod coupled to a proximal end of the puncturing needle, the heart valve repair method comprising:
   advancing a distal end of the suture implanting apparatus from an outside of a body through a transapical approach into a left ventricle or a right ventricle of a heart;
   pushing the capturing rod to separate the distal clamp from the proximal clamp and holding each leaflet of a heart valve using the distal clamp and the proximal clamp;
   pushing the puncturing rod to drive the puncturing needle to puncture the leaflet and couple to the corresponding fixing member of the suture after puncturing through the leaflet;
   withdrawing the puncturing rod to drive the fixing member and the suture through the leaflet to implant the suture into the leaflet; and
   withdrawing the distal end of the suture implanting apparatus from the body.

2. The heart valve repair method according to claim 1, wherein the heart valve repair method further comprises:
   adjusting a length of the sutures remaining in the heart; and
   fixing proximal ends of the sutures to a ventricular wall or a papillary muscle.

3. The heart valve repair method according to claim 1, wherein the suture implanting apparatus further comprises a detecting assembly, the detecting assembly comprises at least one probe, and the at least one probe movably drills through the pushing shaft, the heart valve repair method further comprises:
   using the probe to detect a current clamping state of the leaflet;
   implanting the suture into the leaflet when the probe detects that the current clamping state of the leaflet is an effective clamping state.

4. The heart valve repair method according to claim 3, wherein the heart valve repair method further comprises:
   re-adjusting a position between the distal clamp and the proximal clamp such that there is a certain distance between the distal clamp and the proximal clamp;
   re-adjusting a relative position between the capturing rod and the leaflet, and clamping the leaflet again through the distal clamp and the proximal clamp when the probe detects that the current clamping state of the leaflet is an ineffective clamping state;
   detecting the current clamping state of the leaflet again using the probe; and
   implanting the suture into the leaflet until the probe detects that the current clamping state of the leaflet is the effective clamping state.

5. The heart valve repair method according to claim 4, wherein the suture implanting apparatus further comprises a gripping auxiliary assembly, the gripping auxiliary assembly drills through a lumen of the pushing shaft, the heart valve repair method also comprises:
   pushing the gripping auxiliary assembly to support the leaflet before pushing the capturing rod to separate the distal clamp from the proximal clamp and clamping each leaflet; and
   auxiliary supporting the leaflet using the gripping auxiliary assembly to prevent the leaflet from slipping out between the distal clamp and the proximal clamp in the process of re-adjusting the clamping position of the leaflet.

6. The heart valve repair method according to claim 1, wherein the suture is provided with an anti-slip member, and the anti-slip member comprises a contact surface that is attached to the leaflet, the heart valve repair methods also comprises:
   the anti-slip member not passing through the leaflet and the contact surface of the anti-slip member fitting an upper surface of the leaflet fit when the puncturing rod is withdrawn to drive the fixing member and the suture through the leaflet.

* * * * *